US006998234B2

(12) United States Patent
Fruehauf et al.

(10) Patent No.: US 6,998,234 B2
(45) Date of Patent: Feb. 14, 2006

(54) METHODS FOR CANCER PROGNOSIS AND DIAGNOSIS RELATING TO TUMOR VASCULAR ENDOTHELIAL CELLS

(75) Inventors: John P. Fruehauf, Tustin, CA (US); Eugene Mechetner, Irvine, CA (US)

(73) Assignee: Oncotech, Inc., Tustin, CA (US)

( * ) Notice: Subject to any disclaimer, the term of this patent is extended or adjusted under 35 U.S.C. 154(b) by 517 days.

(21) Appl. No.: 10/144,142

(22) Filed: May 10, 2002

(65) Prior Publication Data

US 2003/0096261 A1 May 22, 2003

Related U.S. Application Data

(63) Continuation-in-part of application No. 09/705,320, filed on Nov. 3, 2000, now Pat. No. 6,511,806.

(51) Int. Cl.
*C12Q 1/68* (2006.01)
*C12P 21/06* (2006.01)
*G01N 33/53* (2006.01)
*G01N 33/574* (2006.01)

(52) U.S. Cl. .......................... 435/6; 435/7.2; 435/7.23; 435/69.1

(58) Field of Classification Search ..................... 435/6, 435/69.1, 7.2, 7.23
See application file for complete search history.

(56) References Cited

U.S. PATENT DOCUMENTS

| | | | |
|---|---|---|---|
| 4,996,145 A | 2/1991 | Weisenthal | |
| 5,464,753 A | 11/1995 | Chaudhary et al. | |
| 5,736,129 A | * 4/1998 | Medenica et al. | 424/85.4 |
| 5,776,747 A | 7/1998 | Aebischer et al. | |
| 5,994,088 A | 11/1999 | Mechetner et al. | |
| 6,004,755 A | 12/1999 | Wang | |
| 6,036,955 A | * 3/2000 | Thorpe et al. | 424/136.1 |
| 6,040,138 A | 3/2000 | Lockhart et al. | |
| 6,165,709 A | 12/2000 | Friend et al. | |
| 6,333,155 B1 | 12/2001 | Lockhart et al. | |
| 6,376,169 B1 | 4/2002 | Adams et al. | |

FOREIGN PATENT DOCUMENTS

WO    WO 99/50401    10/1999

OTHER PUBLICATIONS

Borgiani et al., "Comparative DNA analysis of breast cancer by flow cytomertry and image analysis," Pathologica (Genoa), 86(4):356–359, 1994.
Chen and Huang, "Effect of curcumin on cell cycle progression and apoptosis in vascular smooth muscle cells," British Journal of Pharmacology, 124(6):1029–1040, 1998.
Cordon–Cardo, "Immunohistochemical Analysis of P–Glycoprotein Expression in Normal and Tumor Tissues in Humans," Molecular and Cellular Biology of Multidrug Resistance in Tumor Cells, pp. 303–318, 1991.
Gottesman et al., "Expression of the MDR1 Gene in Normal Human Tissues," Molecular and Cellular Biology of Multidrug Resistance in Tumor Cells, Plenum Press, NY, pp. 279–289, 1991.
Lebow et al., "Analysis of Lymphocyte–Target Conjugates by Flow Cytometry I. Discrimination Between Killer and Non–Killer Lymphocytes Bound to Targets and Sorting of Conjugates Containing One or Multiple Lymphocytes," Natural Immunity and Cell Growth Regulation, 5(5):221–237, 1986.
Mechetner et al., "Levels of Multidrug resistance (MDR1) P–glycoprotein expression by human breast cancer correlate with in vitro resistance to taxol and doxorubin," Clin. Cancer Res., 4:389–98, 1998.
Orfao et al., "A new method for the analysis of plasma cell DNA content in multiple myeloma samples using a CD38/propidium iodide double staining technique," Cytometry, 17(4):332–339, 1994.
Pepper et al., "BCL–2/BAX Ratios in chronic lymphocytic Leukaemia and their correlation with in vitro apoptosis and clinical resistance," British Journal of Cancer, 76(7):935–938, 1997.
Seidl et al., "Evaluation of membrane physiology following flurscence activated or magnetic cell separation," Cytometry, 36(2):102–111, 1999.
Arends et al., "Apoptosis. The role of the endonuclease," Am. J. Pathol. 136(3):593–608, 1990.
Auerbach et al., "From Primitive Embryonic Precursor Cells To Organ And Tumor–Specific Vascular Endothelial Cells: A Progress Report," Proc. Annu. Meet Am. Assoc. Cancer Res. 35:663, 1994.
Bange et al., "Molecular targets for breast cancer therapy and prevention," Nat. Med. 7(5):548–552, 2001.
Battegay, "Angiogenesis: mechanistic insights, neovascular diseases, and therapeutic prospects," J. Mol. Med. 73(7):333–346, 1995.
Benelli et al., "In vitro models of angiogenesis: the use of Matrigel," Int. J. Biol. Markers 14(4):243–246, 1999.
Bertram, "The molecular biology of cancer," Mol. Aspects Med. 21(6):167–223, 2000.

(Continued)

*Primary Examiner*—Kenneth R. Horlick
*Assistant Examiner*—Joyce Tung
(74) *Attorney, Agent, or Firm*—McDonnell Boehnen Hulbert & Berghoff LLP

(57) ABSTRACT

The invention provides methods for prognosis, diagnosis, staging and disease progression in human cancer patients related to expression levels of a plurality of genes that are differentially expressed in anti-angiogenic agent-sensitive and anti-angiogenic agent-resistant vascular endothelial cells as compared to baseline vascular endothelial cells.

7 Claims, 17 Drawing Sheets

OTHER PUBLICATIONS

Bichsel et al., "Cancer proteomics: from biomarker discovery to signal pathway profiling," Cancer J. 7(1):69–78, 2001.

Bussolino e tal., "Molecular mechanisms of blood vessel formation," Trends Biochem. Sc. 22(7):251–256, 1997.

Conrad–Lapostolle et al., "Optimization of use of UEA–1 magnetic beads for endothelial cell isolation," Cell Biol. Toxicol. 12(4–6):189–197, 1996.

Coombes et al., "cDNA Array Analysis of Altered Gene Expression in Human Endothelial Cells in Response to Chlamydia pneumoniae Infection," Infect. Immunol. 69(3):1420–1427, 2001.

Diez et al., "Isolation of full–size mRNA from cells sorted by flow cytometry," J. Biochem. Biophys. Methods 40(3):69–80, 1999.

Emmert–Buck et al., "Molecular Profiling of Clinical Tissue Specimens: Feasibility and Applications," J. Mol. Diagn. 2(2):60–66, 2000.

Feng et al., "Transcriptional Profile of Mechanically Induced Genes in Human Vascular Smooth Muscle Cells," Circ. Res. 85:1118–1123, 1999.

Folkman et al., "Angiogenesis," J. Biol. Chem. 267(16):10931–10934, 1992.

Folkman, "Angiogenesis in cancer, vascular, rheumatoid and other disease," Nat. Med. 1(1):27–31, 1995.

Gargett et al., "Isolation, characterization and long–term culture of human myometrial microvascular endothelial cells," Hum. Reprod. 15(2):293–301, 2000.

Hewett et al., "Human microvessel endothelial cells: isolation, culture and characterization," In Vitro Cell Dev. Biol. 29A(11):823–830, 1993.

Brunstein et al., "The biology and treatment of chronic myelogenous leukemia," Oncology 15:23–31, 2001.

Ingber, "Fibronectin Controls Capillary Endothelial Cell Growth by Modulating Cell Shape," Proc. Nat'l Acad Sci. USA 87:3579–3583, 1990.

Joki et al., "Assessment of alterations in gene expression in recurrent malignant glioma after radiotherapy using complementary deoxyribonucleic acid microarrays," Neurosurgery 48(1):195–202, 2001.

Jones et al., "The Current Status of Clinical Trials in Anti–Angiogenesis," Principles and Practices of Oncology Updates 14(1):1–9, 2000.

Koong et al., "Candidate Genes for the Hypoxic Tumor Phenotype," Cancer Res. 60:883–887, 2000.

Kumar et al., "CD 105 and angiogenesis," J. Pathol. 178(4):363–366, 1996.

Laird et al., "SU6668 is a Potent Antiangiogenic and Anti-tumor Agent That Induces Regression of Established Tumors," Cancer Res. 60:4152–4160, 2000.

Li et al., "Blood–brain barrier genomics," J. Cereb. Blood Flow Metab. 21(1):61–68, 2001.

Li et al., "Positive and negative hematopoietic cytokines produced by bone marrow endothelial cells," Cytokine 12(7):1017–1023, 2000.

Martoglio et al., "Changes in tumorigenesis– and angiogenesis–related gene transcript abundance profiles in ovarian cancer detected by tailored high density cDNA arrays," Mol. Med. 6(9):750–765, 2000.

Matsuno et al., "Induction of Lasting Complete Regression of Preformed Distinct Solid Tumors by Targeting the Tumor Vasculature Using Two New Anti–Endoglin Monoclonal Antibodies," Clin. Cancer Res. 5:371–382, 1999.

Mechetner et al., "Gene Array Analysis of Endothelial Cells Isolated from Human Tumors: A New Approach to the Development of Antiangiogenesis Therapies," Proc. Annu. Meet Am. Assoc. Cancer Res. 42:566–567, 2001.

Mendel et al., "Development of SU5416, a selective small molecule inhibitor of VEGF receptor tyrosine kinase activity, as an anti–angiogenesis agent," Anticancer Drug Design 15(1):29–41, 2000.

Norris et al., "Serum enhancement of human endothelial cell attachment to and spreading on collagens I and IV does not require serum fibronectin or vitronectin," J. Cell Sci. 95(2):255–262, 1990.

Pitas et al., "Uptake of Chemically Modified Low Density Lipoproteins in Vivo is Mediated by Specific Endothelial Cells," J. Cell. Biol. 100:103–117, 1985.

Raynal et al., "Annexins: the problem of assessing the biological role for a gene family of multifunctional calcium– and phospholipid–binding proteins," Biochem. Et Biophys. Acta. 1197(1):63–93, 1994.

Rosfiord et al., "Application of flow cytometry in the analysis and sterile sorting of cell populations based on integrin expression," Methods Mol. Biol. 129:79–90, 1999.

Saaristo et al., "Mechanisms of angiogenesis and their use in the inhibition of tumor growth and metastasis," Oncogene 19(53):6122–6129, 2000.

Schnitzer et al., "Vascular Targeting as a Strategy for Cancer Therapy," New England J. Med. 339(7):472–474, 1998.

Sen et al., "Copper–induced vascular endothelial growth factor expression and wound healing," Am. J. Physiol. Heart Circ. Phyusiol. 282:H1821–7, 2002.

Shibata, "The SURF technique. Selective genetic analysis of microscopic tissue heterogeneity," Methods Mol. Biol. 92:39–47, 1998.

St. Croix et al., "Genes Expressed in Human Tumor Endothelium," Science 289:1197–1202, 2000.

Tabata et al., "Antiangiogenic radioimmunotherapy of human solid tumors in SCID mice using $^{125}$I–labeled anti-endoglin monoclonal antibodies," Int. J. Cancer 82(5):737–742, 1999.

Vasile et al., "Differential expression of thymosin β–10 by early passage and senescent vascular endothelium is modulated by VPF/VEGF: evidence for senescent endothelial cells in vivo at sites of atherosclerosis," FASEB 15:458–466, 2001.

Voura et al., "Cell–cell interactions during transendothelial migration of tumor cells," Microsc. Res. Tech. 43(3):265–275, 1998.

Yamasaki et al., "Genomic instability in multistage carcinogenesis," Toxicol. Lett. 112–113:251–256, 2000.

Zhang et al., "Microarray analysis of nicotine–induced changes in gene expression in endothelial cells," Physiol. Genomics 5:187–192, 2001.

Gottesman et al., "Multidrug Resistance," Annu. Rev. Med. 42:277–86, 1991.

Gudkov et al., "Isolation of Genetic Suppressor Elements, Inducing Resistance to Topoisomerase II–Interactive Cytotoxic Drugs, from Human Topoisomerase II cDNA," Proc. Natl. Acad. Sci. USA, 90:3231–3235, 1993.

Hibi et al., "Human monoclonal antibody recognizing liver–type aldolase B," Biochem J. 240(3):847–56, Dec. 15, 1986.

[Data Sheet, Mouse Monoclonal 4E3, Signet Laboratories, Inc., 2 pages.].

Kern et al., "Highly specific prediction of antineoplastic drug resistance with an in vitro assay using suprapharmacologic drug exposures," J. Nat. Cancer Inst., 82:582–588, 1990.

Maino et al., "Rapid flow cytometric method for measuring lymphocyte subset activation," Cytometry, 20:127–133, 1995.

Scheper et al., Monoclonal antibody JSB–1 detects a highly conserved epitope on the P–glycoprotein associated with multi–drug resistance, Int J Cancer 42(3):389–94, Sep. 1, 1988. [Data Sheet, Mouse Monoclonal JSB1, Signet Laboratories, Inc., 2 pages.].

Data Sheet, Mouse Monoclonal 4E3, Signet Laboratories, Inc., 2 pages. (do not print it).

Data Sheet, Mouse Monoclonal JSB1, Signet Laboratories, Inc., 2 pages. (do not print it).

Gudkov et al., "Isolation of Genetic Suppressor Elements, Inducing Resistance to Topoisomerse II–Interactive Cytotoxic Drugs, from Human Topoisomerase II cDNA," Proc. Natl. Acad. Sci. USA, 90:3231–3235, 1993.

Kern et al., "Highly specific prediction of antineoplastic drug resistance with an in vitro assay using suprapharmacologic drug exposures," J. Nat. Cancer Inst., 82:582–588, 1990.

Maino et al., "Rapid flow cytometric method for measuring lymphocyte subset activation," Cytometry, 20:127–133, 1995.

Winters, "Gene targeted agents: new opportunities for rational drug development," Curr. Opin. Mol. Ther. 2(6):670–681, 2000.

* cited by examiner

A B C

A B

A B

C  D

A

Taxotere, 10μM / Taxotere, 1μM
Taxotere, 0.1μM / Taxotere, 0.01μM
Taxotere, 0.001μM / Control

B

Thalidomide, 10μM / Thalidomide, 1μM
Thalidomide, 0.1μM / Thalidomide, 0.01μM
Thalidomide, 0.001μM / Control

E                F 1  2  3  4

METHODS FOR CANCER PROGNOSIS AND DIAGNOSIS RELATING TO TUMOR VASCULAR ENDOTHELIAL CELLS

This is a Continuation Divisional Continuation-in-part of prior application Ser. No. 09/705,320 filed Nov. 3, 2009 now U.S. Pat. No. 6,511,806.

BACKGROUND OF THE INVENTION

1. Field of the Invention

The invention relates to cancer diagnosis and treatment, and specifically to the determination of an angiogenic phenotype of vascular endothelial cells from cancer patients. The invention specifically relates to the separation of vascular endothelial cells from non-endothelial cells, particularly tumor cells, in human tumor samples. The invention in particular relates to the identification of genes that are differentially expressed in anti-angiogenic agent-sensitive vascular endothelial cells compared with the expression of these genes in anti-angiogenic agent-resistant vascular endothelial cells, or compared to the expression of these genes in vascular endothelial cells that are not exposed to the drug. As part of this identification, the invention provides a pattern of expression from a selected number of identified genes, the expression of which is increased or decreased in anti-angiogenic agent-resistant vascular endothelial cells. The invention provides methods for identifying such genes and expression patterns of such genes and using this information to identify new gene targets for rational drug design, to identify new anti-angiogenic agents, and to make clinical decisions on cancer treatment, especially chemotherapeutic drug treatment of cancer patients.

2. Summary of the Related Art

Cancer remains one of the leading causes of death in the United States. Clinically, a broad variety of medical approaches, including surgery, radiation therapy and chemotherapeutic drug therapy are currently being used in the treatment of human cancer (see the textbook *CANCER: Principles & Practice of Oncology*, 6th Edition, De Vita et al., eds., J. B. Lippincott Company, Philadelphia, Pa.,2001). However, it is recognized that such approaches continue to be limited by a fundamental inability to accurately predict the likelihood of clinically successful outcome, particularly with regard to the sensitivity or resistance of a particular patient's tumor to a chemotherapeutic agent or combinations of chemotherapeutic agents.

A broad variety of chemotherapeutic agents are used in the treatment of human cancer. These include the plant alkaloids vincristine, vinblastine, vindesine, and VM-26; the antibiotics actinomycin-D, doxorubicin, daunorubicin, mithramycin, mitomycin C and bleomycin; the antimetabolites methotrexate, 5-fluorouracil, 5-fluorodeoxyuridine, 6-mercaptopurine, 6-thioguanine, cytosine arabinoside, 5-aza-cytidine and hydroxyurea; the alkylating agents cyclophosphamide, melphalan, busulfan, CCNU, MeCCNU, BCNU, streptozotocin, chlorambucil, bisdiamminedichloroplatinum, azetidinylbenzoquinone; and the miscellaneous agents dacarbazine, mAMSA and mitoxantrone (Id., DeVita et al.).

However, some neoplastic cells become resistant to specific chemotherapeutic agents, in some instances even to multiple chemotherapeutic agents, and some tumors are intrinsically resistant to certain chemotherapeutic agents. Such drug resistance or multiple drug resistance can theoretically arise from expression of genes that confer resistance to the agent, or from lack of expression of genes that make the cells sensitive to a particular anticancer drug. One example of the former type is the multidrug resistance gene, MDR1, which encodes an integral plasma membrane protein termed P-glycoprotein that is a non-specific, energy-dependent efflux pump. (See Roninson (ed)., 1991, *Molecular and Cellular Biology of Multidrug Resistance in Tumor Cells*, Plenum Press, N.Y., 1991; Gottesman et al., 1991, in *Biochemical Bases for Multidrug Resistance in Cancer*, Academic Press, N.Y., Chapter 11 for reviews). Examples of the latter type include topoisomerase II, the expression of which makes cells sensitive to the anticancer drug etoposide. Decreased expression of this enzyme makes neoplastic cells resistant to this drug. (See Gudkov et al., 1993, *Proc. Natl. Acad. Sci. USA* 90: 3231–3235). Although these are just single examples of the way that modulation of gene expression can influence chemotherapeutic drug sensitivity or resistance in neoplastic cells, these examples demonstrate the diagnostic and prognostic potential for identifying genes the expression of which (or the pattern of gene expression modulation thereof) are involved in mediating the clinical effectiveness of anticancer drug treatment.

Drug discovery programs have evolved to include rational therapeutic development strategies in addition to traditional empirical screening approaches. Rational therapy development focuses on the identification of specific pathways that are differentially activated in cancer cells compared to normal tissue (Bichsel et al., 2001, *Cancer J.* 7: 69–78; Winters, 2000, *Curr. Opin. Mol. Ther.* 2: 670–681). Such selective targeting can significantly reduce therapy-associated toxicity. Recent examples where this approach has led to the successful development of new anti-cancer agents include targeting HER2 with Herceptin (Bange et al., 2001, *Nat. Med.* 7: 548–552) in breast cancer and Gleevec's (STI571) inhibition of the BCR-ab1 kinase fusion protein in chronic myeloid leukemia (2001, *Oncology (Huntingt)* 15: 23–31).

Unfortunately, cancer specific pathways are not universal to the transformation process. Transformation results from a variety of alterations in tumor suppressor genes, oncogenes, translocations, deletions and mutations. The genomic instability inherent to this pleiotropic background of metabolic alterations results in significant phenotypic heterogeneity within each tumor (Bertram, 2000, *Mol. Aspects Med.* 21: 167–223; Yamasaki et al., 2000, *Toxicol. Lett.* 112–113: 251–256). Treatment targets are therefore unstable, leading to intrinsic and acquired resistance to rationally designed agents.

Angiogenesis, on the other hand, is a highly regulated process controlled by conserved gene cassettes (Folkman et al., 1992, *J. Biol. Chem.* 267: 10931–10934; Battery et al., 1995, *J. Mol. Med.* 73: 333–346). Recruitment of resting vascular endothelial cells ("VEC") in response to the increased metabolic demands of a growing tumor mass follows stable pathways that are normally invoked in wound healing, reproductive physiology, and in ontogeny (Sen et al., 2002, *Am. J. Physiol. Heart Circ. Physiol.* 282: H1821–7) Thus, evaluation of these pathways offers a distinct advantage for rational therapeutic design because of their intrinsic stability (Schnitzer et al., 1998, *New England J. Med.* 339: 472–474; Jones et al., 2000, *Principles and Practices of Oncology Updates* 14:1–9).

Although mechanisms of angiogenesis in normal tissues have been extensively studied using traditional molecular biology, biochemical and immunological methods (reviewed in Saaristo et al., 2000, *Oncogene* 19: 6122–6129), the prior art contains sparse disclosure relating to differential gene expression in VECs. Li et al. (2001, *J.*

Cereb. Blood Flow Metab. 21: 61–68) developed a protocol for purifying mRNA from isolated normal rat brain capillaries and subsequent microarray analysis of genes selectively expressed in the blood-brain barrier. They identified a series of over 40 novel gene sequences and known genes, including tissue plasminogen activator (TPA), insulin-like growth factor-2, regulators of G protein signaling, etc.), that had not been known to be specific for the blood-brain barrier functions. Similar experiments on normal bone marrow VEC using Atlas cDNA gene arrays showed the presence of mRNAs of several hematopoietic stimulators, cytokines and interleukins, in these cells (Li et al., 2000, *Cytokine* 12: 1017–1023). cDNA microarray analysis of 268 human VEC genes following infection with *Chlamydia pneumoniae* compared with uninfected endothelial cells revealed 20 genes up-regulated in response to *C. pneumoniae* infection, including cytokines (IL-1), chemokines (IL-8, monocyte chemotactic protein 1), and cellular growth factors, including basic fibroblast growth factor (bFGF) and epidermal growth factor (EGF) (Coombes et al., 2001, *Infect. Immunol.* 69: 1420–1427). Microarray-based evaluation of transcriptional profiles of mechanically induced genes in normal human aortic VEC using vascular endothelial growth factor (VEGF) as a positive control identified 3 out of 5000 transcripts up-regulated in these cells (cyclooxygenase-1, tenascin-C, and TPA-1; Feng et al., 1999, *Circ. Res.* 85:1118–1123). Down-regulated genes included thrombomodulin and matrix metalloproteinase-1 (MMP). Recently, Zhang et al. (*Physiol. Genomics* 5: 187–192) utilized the cDNA microarray approach to ascertain gene expression profiles of human coronary artery VEC treated with nicotine. Their analysis of over 4,000 genes identified a number of nicotine-modulated genes involved in signal transduction and transcriptional regulation. Changes in gene expression profiles associated with endothelial senescence have been investigated using cDNA array hybridization with mRNA isolated from late vs. early passages of dermal VEC (Vasile et al., 2001, *FASEB* 15: 458–466). The study results suggest that the expression of thymosin beta-10, a G-sequestering peptide involved in actin regulation, was strongly down regulated in senescent endothelial cells.

Despite this prior art, patterns of gene expression in tumor derived VEC remain poorly described. A group of hypoxia-induced genes that included TPA-1, insulin-like growth factor-binding receptor, endothelin-2, low-density lipoprotein-like receptor-related protein and some other markers of endothelial cells, were identified using cDNA microarrays hybridized with mRNA from two squamous cell carcinoma-derived tumor cell lines (Koong et al., 2000, *Cancer Res.* 60: 883–887). Joki et al. (2001,*Neurosurgery* 48: 195–201) utilized microarray technology to evaluate the effects of radiotherapy on gene expression in glioblastoma multiforme, and in particular, expression of those genes the products of which might influence the biology of neighboring tumor VEC. This reference disclosed decreased expression of growth factors participating in paracrine loops, such as VEGF and platelet-derived growth factor (PDGF) receptor beta, in four post-radiation recurrent tumors and correlated these changes with decreased microvessel counts in these tumors. A 332-membered human cDNA array was used to assess tumorigenesis- and angiogenesis-related patterns of gene expression in five normal ovary and four poorly differentiated serous papillary ovarian adenocarcinoma samples (Martoglio et al., 2000, *Mol. Med.* 6: 750–765). The transcription profiles analysis revealed an overall increase in angiogenesis-related markers, such as VEGF and angiopoietin-1 in tumor specimens. These changes were accompanied by the up-regulation of apoptotic/neoplastic markers (e.g., BAD, b-myb), immune response mediators (e.g., HLA-DR), and ovarian-specific biomarkers (e.g., cofilin, moesin, etc.). However, direct analysis of VEC that were physically isolated from tumor samples was not performed in these studies.

The most comprehensive large-scale analysis of gene expression in tumor-derived VEC was performed by St. Croix et al., who utilized SAGE libraries of approximately 193,000 14-base pair tags derived from a specific position near the 3' termini of individual mRNA transcripts and corresponding to 32,500 unique transcripts (St. Croix et al, 2000, *Science* 289: 1197–1202). VEC were purified from dissociated human colorectal tumors using a two-step immunomagnetic beads base selection protocol including (i) negative selection of epithelial and hematopoietic cell populations on the basis of membrane antigenic markers, and (ii) positive selection of VEC based on the membrane binding of endothelial-specific P1H12 monoclonal antibody (mAb). The expression of candidate transcripts was confirmed by IHC and RT-PCR analyses. The authors reported a series of tags corresponding to either known or unknown genes that provided a first definitive molecular characterization of VEC derived from colorectal tumors. The top 25 tags with the highest tumor EC to normal EC ratios included several MMPs, collagens types I and III, enactin, cystatin S, endo 180 lectin, as well as several expression sequence tags (EST's) corresponding to yet unknown genes. Although gene expression was examined by St. Croix et al. in highly purified tumor VEC populations, no cDNA microarray experiments were performed in this study.

Gene array technologies have not been successfully applied to the analysis of tumor-derived VEC. Several issues have complicated cDNA microarray-based gene expression studies of endothelial cells in vitro. Obtaining pure cell populations from tumor biopsy specimens has been difficult because of the diverse mixture of cells that make up tumors, such as malignant, stromal and blood components (Emmert-Buck et al., 2000, *J. Mol. Diagn.* 2: 60–66). Additionally, VEC represent only a small fraction of the cells comprising the tumor sample. As a result, extracted RNA has been representative of a mixture of the cellular subsets, making it difficult to attribute specific gene expression patterns to the malignant component. There have been unsuccessful attempts in the art to purify target cells including laser capture microdissection, selective protection of malignant cells from irradiation, magnetic beads and flow cytometry (Shibata, 1998, *Methods Mol. Biol.* 92: 39–47; Conrad-Lapostolle et al., 1996, *Cell Biol. Toxicol.* 12: 189–197; Rosfiord et al., 1999, *Methods Mol. Biol.* 129: 79–90; Diez et al., 1999, *J. Biochem. Biophys. Methods* 40: 69–80; Auerbach et al., 1994, *Proc. Annu. Meet Am. Assoc. Cancer Res.* 35: 663).

Thus, there is a need in this art for developing methods for obtaining pure VEC populations from tumor biopsy samples, and for identifying gene expression patterns of VEC that are either sensitive or resistant to anti-angiogenesis agents, in order to identify agents that will be effective against angiogenesis. There is also a need for methods that provide additional information to physicians and cancer patients to enable more informed and individualized treatment decisions, particularly information relating to the usefulness of treating a cancer patient with anti-angiogenesis agents, thereby informing both physician and patient about the treatment methods that have the greatest likelihood of producing a positive outcome.

SUMMARY OF THE INVENTION

The present invention provides methods identifying genes and patterns of gene expression that are characteristic of angiogenic vascular endothelial cells and that are predictive of the clinical effectiveness of anti-angiogenesis drug treatment therapies.

In a first aspect, the invention provides a method for separating vascular endothelial cells from non-vascular endothelial cells in a mixed population of cells, the method comprising the steps of:
  (a) contacting a mixed population of cells with a vital stain or fluorescent dye;
  (b) contacting the mixed population of cells with a detectable immunological reagent that specifically binds to vascular endothelial cells; and
  (c) selecting the cells in the mixed population of step (b) that are not stained with the vital stain or fluorescent dye and that bind the immunological reagent.

In a preferred embodiment, the immunological reagent is a VEC-specific antibody. More preferably, the immunological reagent binds to CD31 or CD105 antigen and the cells are selected by immunomagnetic separation or by fluorescence activated cell sorting. In certain embodiments, the cells are stained with propidium iodide. In certain embodiments, the cells are selected based on their failure to bind to a second detectable immunological reagent, preferably a second detectable immunological reagent that binds to markers specific for non-vascular endothelial cells, such as CD45. In other embodiments, the mixed population of cells is from a tumor sample, preferably a solid tumor sample where the mixed cell population is a disaggregated tumor sample. The cells are selected, for example, using fluorescence activated cell sorting.

In a second aspect, the invention provides a method for determining a gene expression profile of vascular endothelial cells from a mixed population of cells, said method comprising the steps of:
  (a) contacting a mixed population of cells with a vital stain or fluorescent dye;
  (b) contacting said mixed population of cells with a detectable immunological reagent that specifically binds to vascular endothelial cells;
  (c) selecting the cells in said mixed population that bind the immunological reagent and that are not stained with the vital stain of fluorescent dye;
  (d) isolating cellular RNA from the selected cells selected in step (c);
  (e) preparing detectably labeled cDNA or cRNA from the cellular RNA isolated in step (d);
  (f) hybridizing the cDNA or cRNA prepared in step (e) to a gene array comprising a plurality of eukaryotic genes; and
  (g) determining a gene expression profile from the hybridization pattern produced using the cDNA or cRNA preparations in step (f).

In a preferred embodiment, the gene array comprises at least about 100, more preferably at least about 1000, more preferably at least about 2000, more preferably at least about 3000, and more preferably about 8000 known human genes or EST's, and even more preferably at least about 13,000 known human genes. Preferably, the immunological reagent is a VEC-specific antibody, more preferably said reagent binds to CD31 or CD105 antigen. In certain embodiments, the cells are selected by immunomagnetic separation. In other embodiments, the cells are selected by fluorescence-activated cell sorting.

In yet a third embodiment, the invention provides for a method for determining a gene expression profile of vascular endothelial cells from a mixed population after the vascular endothelial cells are exposed to an anti-angiogenic agent, the method comprising the steps of:
  (a) contacting a mixed population of cells with a vital stain or fluorescent dye;
  (b) contacting said mixed population of cells with a detectable immunological reagent that specifically binds to vascular endothelial cells;
  (c) selecting the cells in said mixed population that bind the immunological reagent and that are not stained with the vital stain of fluorescent dye;
  (d) exposing the selected cells of step (c) to an anti-angiogenic agent;
  (e) isolating cellular RNA from the selected cells selected in step (c);
  (f) preparing detectably labeled cDNA or cRNA from the cellular RNA isolated in step (e);
  (g) hybridizing the cDNA or cRNA prepared in step (f) to a gene array comprising a plurality of eukaryotic genes; and
  (h) determining a gene expression profile for the hybridization pattern produced using the cDNA or cRNA preparation in step (g).

In a preferred embodiment, the gene array comprises at least about 100, more preferably at least about 1000, more preferably at least about 2000, more preferably at least about 3000, and more preferably about 8000 known human genes or EST's, and even more preferably at least about 13,000 known human genes. Preferably, the immunological reagent is a VEC-specific antibody, more preferably wherein said reagent binds to CD31 or CD105 antigen. In certain embodiments, the cells are selected by immunomagnetic separation. In other embodiments, the cells are selected by fluorescence-activated cell sorting.

In a fourth embodiment, the invention provides for a method for identifying a gene set that selectively identifies resistance or sensitivity to an anti-angiogenic compound by determining a gene expression profiles of vascular endothelial cells that were cultured in the presence of an anti-angiogenic compound, the method comprising the steps of:
  (a) contacting a mixed population of cells with a vital stain or fluorescent dye;
  (b) contacting said mixed population of cells with a detectable immunological reagent that specifically binds to vascular endothelial cells;
  (c) selecting the cells in said mixed population that bind the immunological reagent and that are not stained with the vital stain of fluorescent dye;
  (d) exposing a first subset of cells selected in step (c) to an anti-angiogenic agent;
  (e) contacting the first subset of cells with a discrimination compound that specifically binds to apoptotic cells;
  (f) selecting the first subset of cells that bind the discrimination compound;
  (g) isolating cellular RNA separately from the first subset of cells and from a second subset of cells selected in step (c);
  (h) preparing detectably labeled cDNA or cRNA separately from the cellular RNA isolated from the first subset of cells and the second subset of cells;
  (i) hybridizing each of the cDNA or cRNA preparations in step (h) to a gene array comprising a plurality of eukaryotic genes;

(j) determining a gene expression profile from the hybridization pattern produced using the cDNA or cRNA preparations;

(k) comparing the gene expression profile detected in step (j) for each of the cDNA preparations; and (l) determining the gene expression profile of apoptotic vascular endothelial cells thereby;

(m) identifying a gene set that selectively identifies resistance or sensitivity to anti-angiogenesis agents.

In a preferred embodiment, the vascular endothelial cells are obtained from a mixed population of cells, most preferably wherein said mixed population comprise tumor cells. Preferably, the gene array comprises at least about 100, more preferably at least about 1000, more preferably at least about 2000, more preferably at least about 3000, and more preferably about 8000 known human genes or EST's, and even more preferably at least about 13,000 known human genes. More preferably, the immunological reagent is a VEC-specific antibody, more preferably wherein said antibody binds to CD31 or CD105 antigen. In certain embodiments, the cells are selected by immunomagnetic separation. In other embodiments, the cells are selected by fluorescence-activated cell sorting. Preferably, the discrimination compound is Annexin V.

In a fifth embodiment, the invention provides for a method for identifying a compound as an anti-angiogenic agent, the method comprising the steps of:

(a) contacting a mixed population of cells with a vital stain or fluorescent dye;

(b) contacting a mixed population of cells with a detectable immunological reagent that specifically binds to vascular endothelial cells;

(c) selecting the cells in said mixed population that bind the immunological reagent and that are not stained with the vital stain of fluorescent dye;

(d) exposing a first subset of the cells selected in step (c) to a compound;

(e) contacting the first subset with a discrimination compound that specifically binds to apoptotic cells;

(f) selecting the first subset of cells that bind the discrimination compound;

(g) isolating cellular RNA separately from the first subset of cells and from a second subset of cells selected in step (c);

(h) preparing detectably labeled cDNA or cRNA separately from the cellular RNA isolated from the first subset of cells and the second subset of cells;

(i) hybridizing each of the cDNA or cRNA preparations in step (h) to a gene array comprising a plurality of eukaryotic genes;

(j) determining a gene expression profile from the hybridization pattern produced using the cDNA or cRNA preparations; and (k) identifying the anti-angiogenic agent when the cDNA or cRNA preparation from the first subset of cells has at least one gene differentially expressed compared with the EDNA or cRNA preparation from the second subset of cells.

In a preferred embodiment, the gene array comprises at least about 100, more preferably at least about 1000, more preferably at least about 2000, more preferably at least about 3000, and more preferably about 8000 known human genes or EST's, and even more preferably at least about 13,000 known human genes. Preferably, the immunological reagent is a VEC-specific antibody, more preferably wherein said antibody binds to CD31 or CD105 antigen. In certain embodiments, the cells are selected by immunomagnetic separation. In other embodiments, the cells are selected by fluorescence-activated cell sorting. Preferably, the discrimination compound is Annexin V.

In a sixth embodiment, the invention provides a method for identifying a tumor angiogenesis gene target for rational therapeutic drug design, the method comprising the steps of:

(a) contacting a mixed population of cells with a vital stain or fluorescent dye;

(b) contacting said mixed population of cells with a detectable immunological reagent that specifically binds to vascular endothelial cells;

(c) selecting the cells in said mixed population that bind the immunological reagent and that are not stained with the vital stain of fluorescent dye;

(d) exposing a first subset of the cells selected in step (c) to an anti-angiogenic agent;

(e) contacting the first subset of cells with a discrimination compound that specifically binds to apoptotic cells;

(f) selecting the first subset of cells that bind the discrimination compound;

(g) isolating cellular RNA from each of the first subset of cells and from a second subset of cells selected in step (c);

(h) preparing detectably labeled cDNA or cRNA from the cellular RNA isolated from each of the first subset of cells and the second subset of cells;

(i) hybridizing each of the cDNA or cRNA preparations in step (h) to a gene array comprising a plurality of eukaryotic genes;

(j) determining a gene expression profile from the hybridization pattern produced using the cDNA or cRNA preparations; and (k) identifying a tumor angiogenesis gene target for rational therapeutic drug design that is a gene that is differentially expressed in vascular endothelial cells exposed to the compound compared with to vascular endothelial cells not exposed to a compound.

In a preferred embodiment, the difference in expression is at least about 2-fold. Preferably, the gene array comprises at least about 100, more preferably at least about 1000, more preferably at least about 2000, more preferably at least about 3000, and more preferably about 8000 known human genes or EST's, and even more preferably at least about 13,000 known human genes. More preferably, the immunological reagent is a VEC-specific antibody, more preferably wherein said antibody binds to CD31 or CD105 antigen. In certain embodiments, the cells are selected by immunomagnetic separation. In other embodiments, the cells are selected by fluorescence-activated cell sorting or flow cytometry. Preferably, the discrimination compound is Annexin V.

In a seventh embodiment, the invention provides a method for identifying a tumor that is responsive to an anti-angiogenic agent, the method comprising the steps of:

(a) obtaining a population of cells comprising cells from a tumor sample, (b) contacting the population of cells with a detectable immunological reagent that specifically binds to vascular endothelial cells;

(c) selecting the cells in said mixed population that bind the immunological reagent;

(d) exposing the selected cells of step (c) to an anti-angiogenic agent;

(e) isolating cellular RNA from the exposed cells of step (d);

(f) preparing detectably labeled cDNA or cRNA from the cellular RNA isolated in step (e);

(g) hybridizing the cDNA or cRNA prepared in step (f) to a gene array comprising a plurality of eukaryotic genes;

(h) determining a pattern of gene expression produced by hybridization of the cDNA or cRNA preparations in step (g); and (i) comparing the pattern of gene expression detected in step (h) with the pattern of gene expression for vascular endothelial cells that are responsive to the anti-angiogenic agent;

wherein the tumor is identified as responsive to the anti-angiogenic agent when the compared patterns are substantially similar. In a preferred embodiment, the tumor sample is a cancer patient tumor sample. Preferably, the gene array comprises at least about 100, more preferably at least about 1000, more preferably at least about 2000, more preferably at least about 3000, and more preferably about 8000 known human genes or EST's, and even more preferably at least about 13,000 known human genes. More preferably, the immunological reagent is a VEC-specific antibody, more preferably wherein said antibody binds to CD31 or CD105 antigen. In certain embodiments, the cells are selected by immunomagnetic separation. In other embodiments, the cells are selected by fluorescence-activated cell sorting. Preferably, the discrimination compound is Annexin V.

It is an advantage of the methods of this invention that enriched or purified vascular endothelial cell populations from solid and hematopoietic tumors, both malignant and benign, can be obtained separated from stromal cells, infiltrating non-neoplastic hematopoietic cells and other tumor components. This feature of the inventive methods are advantageous because the presence of such contaminating, non-vascular endothelial cells in tumor sample preparations confounds analysis directed at detecting vascular endothelial cell-specific properties, such as patterns of gene expression as disclosed herein. It is also an advantage of the present inventive methods that drug-resistant and drug-sensitive vascular endothelial cells can be separated from pure neoplastic cell populations. As a result, RNA preparations specific for drug-resistant and drug-sensitive vascular endothelial cells are obtained that can be used to identify genes, and patterns of genes, that are differentially expressed in drug-resistant and drug-sensitive vascular endothelial cells.

Specific preferred embodiments of the present invention will become evident from the following more detailed description of certain preferred embodiments and the claims.

BRIEF DESCRIPTION OF THE DRAWINGS

FIG. 3A shows isotype control staining with mouse IgG-FITC, mouse IgG-PE, and PI. FIG. 3B shows staining with anti-CD31 FITC-labeled (FL1) mAb, anti-CD105 PE-labeled (FL2), and PI (FL3).

FIG. 6A shows an autofluorescence control and FIG. 6B shows staining with Annexin V-FITC and PI.

FIG. 7B shows that apoptosis has occurred at 24 hours.

FIG. 8A shows the standard dual parameter DNA doublet discrimination display for gating of non-clumped cells. FIG. 8B shows untreated HL-60 cells stained with d-UTP and PI (negative control). FIG. 8C shows HL-60 cells treated with TPA (positive control). FIG. 8D shows HUVEC cultured on collagen I with 1 $\mu$M docetaxel for 48 hours.

FIG. 9B shows an analysis of the cell culture mixture before immunomagnetic sorting based on CD105 antigenstaining. FIG. 9C shows an analysis of positively selected cells after the immunomagnetic separation, while FIG. 9D shows an analysis of negatively selected cells. FIG. 9E shows that the CD105-positve cell population cultured on collagen I retained CD105 antigen expression phenotype.

FIG. 18A shows the results from the VEC cultured with docetaxel, and FIG. 18B shows the results for VEC cultured with BSO. The diagonal lines represent more than a two-fold difference in expression levels.

DETAILED DESCRIPTION OF THE PREFERRED EMBODIMENTS

Figure 1:
FIGS. 1A and 1B are phase contrast photomicrographs of HUVEC monolayers on fibronectin (FIG. 1A) and collagen I (FIG. 1B).
FIG. 1C is a photomicrograph of FITC-based immunofluorescent staining for CD31 antigen of HUVEC monolayers growing on fibronectin.

The present invention provides methods for making a determination about the tumor-derived VEC response to anti-angiogenesis therapy, and the identification of new targets for such therapy. The patient's prognosis can be better understood from knowledge regarding their tumor's response to anti-angiogenesis therapy. The term "prognosis" is intended to encompass predictions and likelihood analysis of disease progression, particularly tumor recurrence, metastatic spread and disease relapse. The prognostic methods of the invention are intended to be used clinically in making decisions concerning treatment modalities, including therapeutic intervention, diagnostic criteria such as disease staging, and disease monitoring and surveillance for metastasis or recurrence of neoplastic disease.

The methods of the invention are preferably performed using human cancer patient tumor samples, most preferably samples obtained from surgical biopsies that are required to make a cancer diagnosis. For the purposes of this invention, the term "tumor sample" is intended to include resected solid tumors, biopsy material, pathological specimens, bone marrow aspirates, malignant ascetic fluid, malignant pleural effusions, as well as benign tumors, particularly tumors of certain tissues such as brain and the central nervous system. One of ordinary skill will appreciate that samples derived from solid tumors will require combinations of physical and chemical/enzymatic disaggregation.

Vascular endothelial cells are separated from dying cells, dead cells and cell debris, and anti-angiogenic agent sensitive and resistant cells are separated from each other and from non-endothelial cells according to the methods of the invention by cell sorting methods, most preferably immunomagnetic separation or fluorescence-activated cell sorting (FACS). Separation of living cells from dying cells, dead cells and cell debris is facilitated by contacting mixed cell populations with a vital stain, preferably a fluorescent vital stain, such as propidium iodide (PI) and ethidium bromide (EtBr). Separation of anti-angiogenic agent sensitive and resistant cells from one another and from non-endothelial cells using reagents that discriminate between such cells. In particular, anti-angiogenic agent resistant endothelial cells are separated from anti-angiogenic agent sensitive endothelial cells after culturing with an anti-angiogenic agent by contacting the mixed cell population with a discrimination compound that specifically binds to apoptotic cells, and separation is achieved using reagents, most preferably detectable immunological agents, that specifically binds to the discrimination compound. In preferred embodiments, the discrimination compound is an annexin, most preferably annexin V.

For the purposes of this invention, the term "immunological reagents" is intended to encompass antisera and antibodies, particularly monoclonal antibodies, as well as fragments thereof (including F(ab), F(ab)$_2$, F(ab)N and F$_V$ fragments). Also included in the definition of immunological reagent are chimeric antibodies, humanized antibodies, and recombinantly-produced antibodies and fragments thereof, as well as aptamers (i.e., oligonucleotides capable of interacting with target molecules such as peptides). Immunological methods used in conjunction with the reagents of the invention include direct and indirect (e.g, sandwich-type) labeling techniques, immunoaffinity columns, immunomagnetic beads, fluorescence activated cell sorting (FACS), enzyme-linked immunosorbent assays (ELISA), and radio-immune assay (RIA), most preferably FACS. For use in these assays, the detectable immunological reagents can be labeled, using fluorescence, antigenic, radioisotopic or biotin labels, among others, or a labeled secondary or tertiary immunological detection reagent can be used to detect binding of the detectable immunological reagents (i.e., in secondary antibody (sandwich) assays).

Examples of detectable immunological reagents useful in the practice of this invention include antibodies, most preferably monoclonal antibodies, that recognize vascular endothelial cells or hematopoietic cells such as, but not limited to, CD31 antigen, CD105 antigen, and CD45. The detectable immunological reagents of the invention are preferably detectably labeled, most preferably using fluorescent labels that have excitation and emission wavelengths adapted for detection using commercially-available instruments such as and most preferably fluorescence activated cell sorters. Examples of fluorescent labels useful in the practice of the invention include phycoerythrin (PE), fluorescein isothiocyanate (FITC), rhodamine (RH), Texas Red (TX), Cy3, Hoechst 33258, and 4', 6-diamidino-2-phenylindole (DAPI). Such labels can be conjugated to immunological reagents, such as antibodies and most preferably monoclonal antibodies using standard techniques (Maino et al., 1995, *Cytometry* 20: 127–133).

As used herein, the terms "microarray", "bioarray", "biochip" and "biochip array" refer to an ordered spatial arrangement of immobilized biomolecular probes arrayed on a solid supporting substrate. Preferably, the biomolecular probes are immobilized on second linker moieties in contact with polymeric beads, wherein the polymeric beads are immobilized on first linker moieties in contact with the solid supporting substrate. Biochips, as used in the art, encompass substrates containing arrays or microarrays, preferably ordered arrays and most preferably ordered, addressable arrays, of biological molecules that comprise one member of a biological binding pair. Typically, such arrays are oligonucleotide arrays comprising a nucleotide sequence that is complementary to at least one sequence that may be or is expected to be present in a biological sample. Alternatively, and preferably, proteins, peptides or other small molecules can be arrayed in such biochips for performing, inter alia, immunological analyses (wherein the arrayed molecules are antigens) or assaying biological receptors (wherein the arrayed molecules are ligands, agonists or antagonists of said receptors). Useful microarrays for detecting differential patterns of gene expression between anti-angiogenic agent sensitive and resistant VEC cells are described, inter alia, in U.S. Pat. No. 6,040,138 to Lockhart et al. (commercially-available from Affymetrix, Inc., Santa Clara, Calif.) and U.S. Pat. No. 6,004,755 to Wang (commercially-available from Incyte Inc., Palo Alto, Calif.) and are also commercially available, inter alia, from Research Genetics (Huntsville, Ala.). An example of commercially available biochips, but not meant to be limiting, is the Affymetrix GeneChip® Human Genome U133 Set (which includes both HG-U133A and HG-U133B).

The practice of one embodiment of the invention involves the gene array analysis of highly purified VEC populations derived from human tumor specimens that are anti-angiogenic agent sensitive compared to VEC that are anti-angiogenic agent resistant. A tumor sample or tumor cell line is harvested and pure VEC populations obtained by immunomagnetic separation or FACS sorting using antibodies specific for VEC (such as anti-CD31 and anti-CD105), and negative selection with antibodies specific for non-VEC (such as antibodies for the pan-hematopoietic marker CD45). The sorted purified VEC cell population is then expanded by growth in cell culture to provide sufficient cells for separation into drug-sensitive and drug-resistant populations. The VEC are exposed to an anti-angiogenic agent in cytophobic plates. Anti-angiogenic agent sensitive VEC are then separated from anti-angiogenic agent resistant VEC, most preferably using fluorescence-activated cell sorting. Cells cultured in anti-angiogenic agent are stained with a fluorescent vital stain such as propidium iodide and contacted with an apoptosis-specific discrimination agent such as a fluorescently labeled immunological reagent that specifically labels the apoptotic, anti-angiogenic agent sensitive VEC. In a preferred embodiment, the discrimination reagent is Annexin V, which binds to phosphatidylserine exposed by apoptosis in anti-angiogenic agent sensitive cells and does not bind to anti-angiogenic agent resistant VEC. FACS analysis is used to separate the anti-angiogenic agent resistant, living cells from cell debris, dead cells (such as stromal cells) and anti-angiogenic agent-sensitive VEC. It is also an advantage of the inventive methods that FACS sorting can discriminate between anti-angiogenic agent sensitive VEC (typically caused to be apoptotic as a result of anti-angiogenic agent treatment), anti-angiogenic agent resistant VEC and dead or dying cells by gating the cell sorter to perform simultaneous discrimination between these different components of the mixed population.

The practice of another embodiment of this invention involves gene array analysis of highly purified VEC populations derived from human tumor specimens at baseline and after exposure to an anti-angiogenic agent. A tumor sample or tumor cell line is harvested and pure VEC populations are obtained by immunomagnetic separation or FACS sorting using antibodies specific for VEC (such as anti-CD31 and anti-CD105), or negative selection with antibodies specific for non-VEC (such as antibodies for the pan-hematopoietic marker CD45). Total RNA is prepared from both a sample of the VEC population before and after exposure to the anti-angiogenic agent. The VEC exposed to the anti-angiogenic agent are isolated using the above method.

Cell sorting according to the methods of the invention provides sufficient numbers of separated VEC to be able to perform gene expression profile analysis. Gene expression profile analysis is performed to detect differences in gene expression profiles between purified populations of VEC. RNA from the VEC is individually isolated and cDNA or cRNA prepared therefrom. In preferred embodiments, the cDNA or cRNA is detectably labeled, for example using radioactively labeled or fluorescently labeled nucleotide triphosphates. Hybridization patterns of gene expression microarrays produces patterns of gene expression specific for VEC. Identification of genes and patterns of genes differentially expressed in these cells is established by comparison of the gene expression profiles obtained by performing the microarray hybridization pattern analysis on cDNA from VEC. Patterns of gene expression specific for VEC, including patterns of gene expression specific for VEC that are anti-angiogenic agent sensitive or resistant, are obtained using the inventive methods.

The following Examples are intended to further illustrate certain preferred embodiments of the invention and are not limiting in nature.

EXAMPLES

Endothelial Tissue Culture

The HUVEC cell line, derived from human umbilical cord vascular endothelial cells, was obtained from ATCC (Manassas, Va.). These cells were used to develop and validate the in vitro culture systems, morphological and functional tests for VEC differentiation and apoptosis assays. To avoid cell senescence and other changes due to prolonged culturing of the cell line, early passages (from 3 to 10) and limited culture periods (from 1 to 3 months) were used. The E-STIM Endothelial Cell Culture Medium (Becton Dickinson, San Jose, Calif.), containing 1 µg/mL hydrocortisone, 10 ng/mL Epidermal Growth Factor (EGF), 200 µg/mL Endothelial Cell Growth Supplement (ECGS), and 10 units/mL heparin, was used in all experiments because it has been proven to be suitable for culturing endothelial cells from a variety of species and tissue types. When the endothelial cells were cultured on collagen I, the E-STIM medium was supplemented with 2% fetal calf serum ("FCS"); and when VEC were cultured on fibronectin or MATRIGEL, the E-STIM medium was supplemented with 20% FCS.

Collagen I has been demonstrated to be the optimal extracellular matrix ("ECM") for promoting rapid proliferation of VEC. (Norris et al., 1990, *J. Cell Sci.* 95:255–262). Preliminary experiments showed that collagen I-treated plastic, in combination with low-serum (2% FCS) E-STIM, provided optimal conditions for proliferating endothelial cells. Therefore, these conditions were used to expand endothelial cultures for gene array and cell-sorting studies. Tissue culture flasks and 2- and 8-well Multiwell Plates (Becton Dickinson) coated with rat-tail collagen I as a substrate for adhesion, growth, and differentiation of VEC were used. Post-culture analysis demonstrated that endothelial cells that were expanded on collagen I-treated flasks expressed VEC-specific antigens (e.g., CD31 antigen, CD105 antigen, and Flk 1) and exhibited functional activities (e.g., DiI-ac-LDL (acetylated low density lipoprotein, labeled with 1,1'-dioctadecyl-3,3,3',3'-tetramethylindocarbocyanine perchlorate) uptake, tubulogenesis, and capillary-like network formation) that are characteristic for VEC.

Antibody-Based Tests for Angiogenesis

Figure 2:
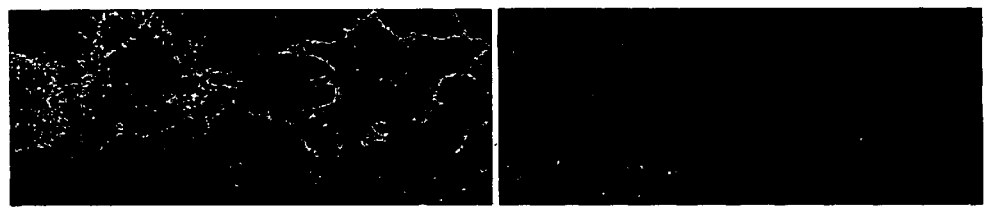
FIGS. 2A and 2B are photomicrographs of immunostained live HUVEC cultured on fibronectin using mAbs against VEC differentiation markers, CD31 antigen(FIG. 2A) and CD105 antigen(FIG. 2B).

To optimize in vitro environments for promoting VEC differentiation and formation of endothelial monolayers demonstrating VEC-specific functional activities, a combination of fibronectin-coated plastic and high-serum (10–20% FCS) E-STIM was used. The spatial orientation of adsorbed fibronectin, a 440–500 kD glycoprotein component of ECM, modulates VEC adhesion and differentiation in vitro. (Ingber, 1990, *Proc. Nat'l Acad. Sci. U.S.A.* 87:3579–3583). Live HUVEC cultured on fibronectin was immunostained using mAbs against VEC differentiation markers CD31 and CD105 antigen. CD31 (PECAM-1, platelet endothelial cell adhesion molecule), a 130 kD membrane glycoprotein that mediates cell-cell adhesion, was immunostained with WM59 mAb (Serotec, Oxford, UK). CD105 (endoglin), a 95 kD membrane marker of activated VEC (Kumar et al., 1996, *J. Pathol.* 178:363–366), was immunostained with SN6 mAb (Serotec). Phycoerythrin (PE)-labeled secondary antibodies against mouse IgG were used to detect primary antibody binding for both markers. Photomicrographs were taken under an immunofluorescent microscope using two different filters converting PE emission spectrum to yellow (CD31 antigen) or red (CD105 antigen) light, and are shown in FIGS. 1 and 2. HUVEC cultured on fibronectin demonstrated a flattened morphology and numerous sprouts and intercellular junctions. CD31 ANTIGEN staining was localized to points of cell-to-cell contacts, which is characteristic for VEC.

Immunophenotyping was also performed by flow cytometry and immunohistochemistry in order to evaluate cell surface expression of CD31 antigen, CD105 antigen, VEGF, VEGF receptor-1 (Flk 1), and CD36 (TSP1 receptor). These markers are known to undergo differential expression during vasculogenesis, and they are potentially associated with different gene expression profiles mirroring differences in phenotype that may be potential surrogates of response to anti-angiogenesis therapy.

In flow cytometry and indirect immunofluorescence analyses, HUVEC were treated with directly or indirectly labeled mAbs as described previously (Mechetner et al, 1998, *Clin. Cancer Res.* 4:389–398, incorporated by reference herein). Data were acquired in the "list" mode on a FACScan or FACSVantage flow cytometer (Becton Dickinson) equipped with 15 milliwatt argon lasers. Fluorescence emission (488 nm excitation) was collected after passing through band pass filters (530/30 nm for FITC, 575/26 for PE, 630/30 or 675/20 for PI). 10,000 events were collected and analyzed on a FACScan/FACSVantage interfaced model 340 Hewlett Packard computer using LYSYS II or Cell Quest software (Becton Dickinson). Live VEC monolayers stained with labeled or unlabeled mAbs against endothelial differentiation markers were analyzed using Optiphot fluorescent microscope (Nikon U.S., Melville, N.Y.) equipped with the B-2A (Nikon) and C-9129 (ChromaVision, San Juan Capistrano, Calif.) filters converting PE fluorescence to yellow or red light, respectively, and the UFX-II camera (Nikon) was used to generate photomicrographs.

WM59 mAb conjugated with FITC (Serotec, Oxford, UK) was used to detect human CD31 antigenon human endothelial cell lines and VEC from human tumor specimens. To identify CD105 antigen, the SN6 mAb labeled with PE (Serotec) was used. CD36 expression was identified with the FA6-152 mAb (Becton Dickinson). Because CD31 and CD105 antigenare also expressed on the surface of several subsets of nucleated hematopoietic cells (granulocytes, lymphocytes, macrophage), precise gating flow cytometry of human VEC was performed including several independent parameters: (1) staining for VEC differentiation markers (e.g., CD31 and/or CD105 antigen); (2) exclusion of nucleated blood cells infiltrating tumor specimens based on staining for CD45, a pan-hematopoietic marker; (3) exclusion of nucleated blood cells and platelets based on cell size and granularity (forward/size scatter gating), and (4) exclusion of dead cells based on the staining with 1 µg/mL PI. Human CD45 was detected in all experiments with the H130 PE-conjugated mouse mAb (PharMingen, San Diego, Calif.).

Figure 3:
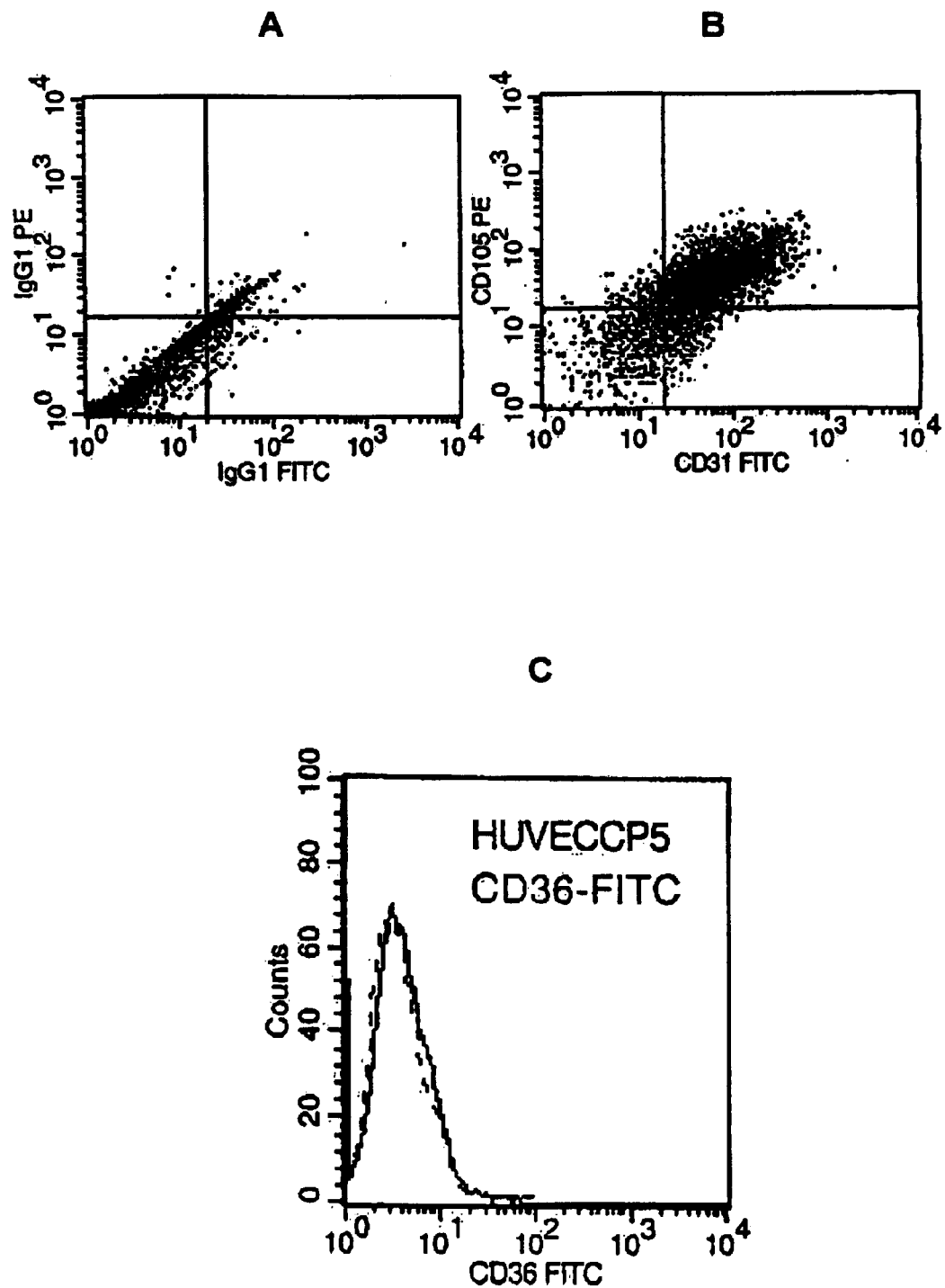
FIGS. 3A and 3B are flow cytometry profiles of HUVEC cells.
FIG. 3C is a graph of a two-color analysis using anti-CD36 mAb and PI.

In addition, three-color flow cytometry analysis of HUVEC was performed. Isotype control staining was performed by using mouse IgG-FITC, mouse IgG-PE, and PE. In addition, cells were stained with anti-CD31 FITC-labeled (FL1) and anti-CD105 PE labeled (FL2) mAbs, and PI (FL3). There was a positive correlation between CD31 and CD105 membrane expression. Two-color analysis was also performed using anti-CD36 mAb and PI. No CD36 expression was detected on HUVEC, as shown in FIG. 3.

Functional Tests for Angiogenesis

Functional tests were also used to characterize the differentiation status of VEC cultured in different growth environments in vitro, as previously described. (Hewett et al., 1993, *In Vitro Cell Dev. Biol.* 29A: 823–830; Benelli et al., 1999, *Int. J. Biol Markers* 14: 243–246). MATRIGEL, a three-dimensional support matrix that is composed of solubilized membranes extracted from Engelbreth-Holm-Swarm ("EHS") mouse sarcoma cells, was used because of the ability of mammalian VEC derived from different tissue sources to form capillary-like tubules and generate branched and forked networks in this media. The major components of this matrix are ECM proteins, such as laminin, collagen IV, entactin, and heparan sulphate proteoglycan, as well as growth factors, such as bFGF and EGF. MATRIGEL has previously been used to induce and maintain differentiation of endothelial, muscle, and neuronal cells, and for the development of three-dimensional matrix and cell invasion systems in vitro. (Gargett et al., 2000, *Hum. Reprod.* 15:293–301; Voura et al., 1998, *Microsc. Res. Tech.* 43: 265–275).

Figure 4:
FIGS. 4A and 4B are photomicrographs of HUVEC tubulogenesis on MATRIGEL after a 3 (FIG. 4A) and 24 (FIG. 4B) hour period of incubation on the surface of the gel.

VEC were cultured both on BIOCOAT MATRIGEL matrix-coated tissue culture flasks (Becton Dickinson), and on MATRIGEL matrix prepared from pre-frozen gels that were thawed, kept at +4° C. before use and solidified at +37° C. for 3–16 hours before testing. The optimal time to detect the formation of tubules and capillary-like networks on MATRIGEL was from 3–6 hours. (Gargett et al., 2000, *Hum. Reprod.* 15:293–301; Voura et al., 1998, *Microsc. Res. Tech.* 43: 265–275). As shown in FIG. 4, very few tubules were observed on MATRIGEL 24 hours after plating. No viable VEC were found in MATRIGEL cultures after 48 hours.

The uptake of Dil-ac-LDL (Biomedical Technologies, Inc., Stoughton Mass.) was utilized to identify and characterize differentiated VEC using fluorescent microscopy on live cell monolayers. After uptake, Dil-ac-LDL is degraded by lysosomal enzymes in endothelial cells, with the Dil fluorescent probe accumulating in the intracellular membrane. (Pitas et al., 1985, *J. Cell. Biol.* 100:103–117). Discrimination using this system is high, because no other cell type, with the exception of macrophages, is labeled to the same degree as VEC (Voura et al, 1998, *Microsc. Res. Tech.* 43: 265–275; Pitas et al., 1985, *J. Cell Biol.* 100:103–117), and macrophages can be excluded from the analysis and sorting protocols with CD45 staining. In addition, macrophages can be differentiated from VEC because the former is more brightly labeled with Dil-ac-LDL.

Figure 5A:
FIG. 5A is an immunofluorescent photomicrograph of HUVEC labeled with Dil-ac-LDL for 4 hours on a fibronectin-treated 2-well Biocoat multi-well plate.
Figure 5B:
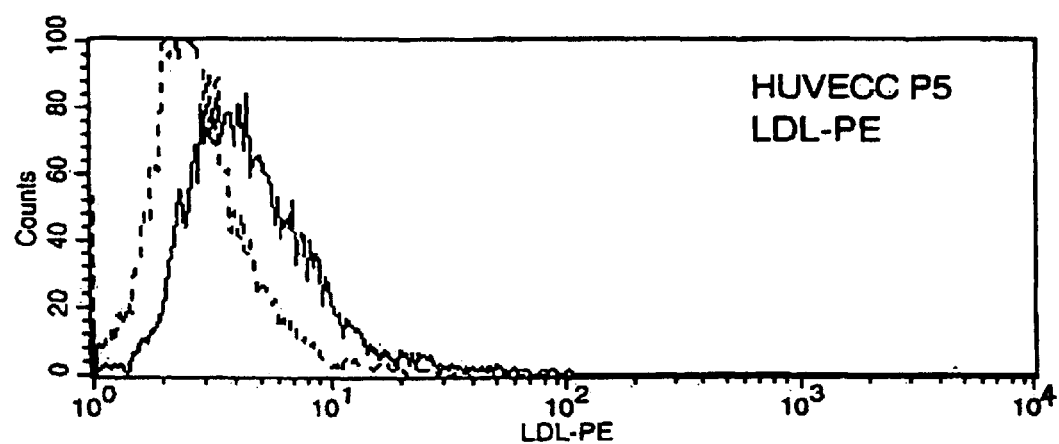
FIG. 5B is a graph of flow cytometry analysis of HUVEC labeled with Dil-ac-LDL.
Figure 6A:
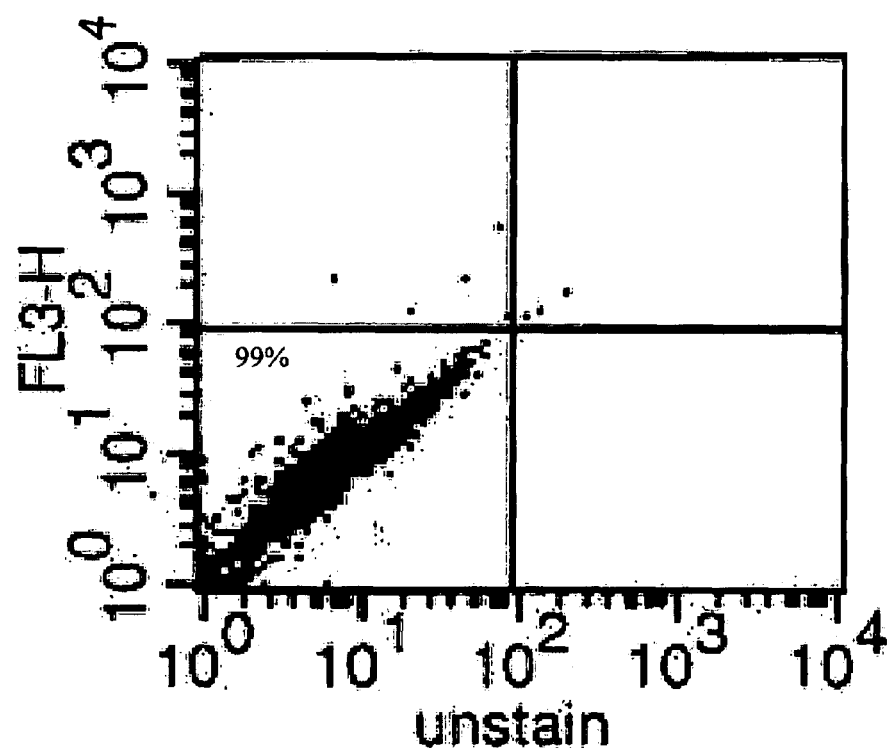
Figure 6B:
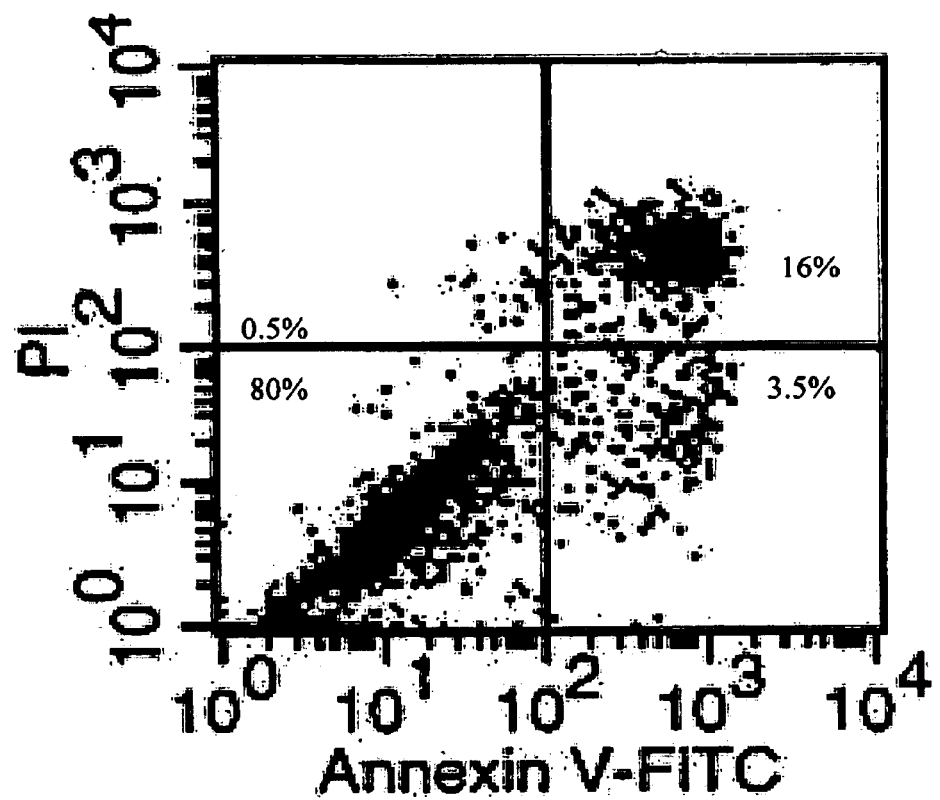

A HUVEC monolayer cultured on fibronectin-treated 2-well BIOCOAT multi-well plates was labeled with Dil-ac-LDL for 4 hours and visualized with immunofluorescent photomicrography; these results are shown in FIG. 5. Dil-ac-LDL was detected as red fluorescence using a C-1929 ChromaVision filter. In addition, flow cytometry analysis was performed on HUVEC labeled with Dil-ac-LDL and PI; dead cells were excluded based on PI staining.

Another human endothelial cell line, HAAE1 endothelial cell line derived from human abdominal aorta and obtained from ATCC, was used to further validate the culture system and morphological and functional tests for VEC differentiation. As described above for HUVEC cells, early passages and limited culture periods were used to avoid cell senescence and other potential modifications due to prolonged culturing of the cell line. With the exception of relatively low TSP-1 expression, the pattern of endothelial antigenic markers in HAEE1 was almost identical to that in HUVEAC (high expression of CD31, CD105, VEGF, Flk 1, and p53; absence of CD36 staining).

Detection of Apoptosis in Endothelial Cells

An in vitro assay was developed to detect apoptotic response after exposure to anti-angiogenesis agents to serve as a surrogate system in screening the activity of these agents. Two flow cytometry-based assays were used to test for VEC apoptosis: (1) the Annexin V staining test for early apoptotic events, and (2) the APO-DIRECT assay based on the detection of DNA breaks related to later stages of apoptosis.

(1) Annexin V Staining Test for Endothelial Cells Undergoing Apoptosis

Altered cell attachment and loss of membrane integrity are among the earliest morphological features of programmed cell death. Annexin V, a 35–36 kDa $Ca^{2+}$-dependent phospholipid-binding protein, has a high affinity for the membrane phospholipid phosphatidylserine, normally located on the inner leaflet of the cell membrane (Raynal et al., 1994, *Biochem. et Biophys. Acta.* 1197:63–93). In cells undergoing apoptosis, however, phosphatidylserine is translocated to the outer leaflet of the plasma membrane and can be detected by Annexin V labeled with fluorescent dyes, such as FITC. To distinguish truly apoptotic cells from necrotic cells, Annexin V was used in combination with PI exclusion. In this assay, HUVEC undergoing apoptosis are Annexin V-positive, PI negative, while necrotic cells are Annexin V-positive, PI-positive.

Figure 6:
FIGS. 6A and 6B are flow cytometry profiles of Annexin V binding of HUVEC cultured on collagen I and treated with docetaxel at 0.001 mM.
FIG. 6C is an immunofluorescent photomicrograph and 6D is a phase contrast photomicrographs of HUVEC cultured on collagen I and treated with docetaxel at 1 $\mu$M and stained with Annexin V-FITC and PI.
Figure 6:
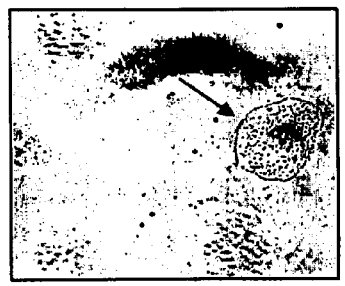
Figure 9F:
FIG. 9F is an immunofluorescent photomicrograph of a CD105-positive cell population that have taken up Dil-ac-LDL.
Figure 7A:
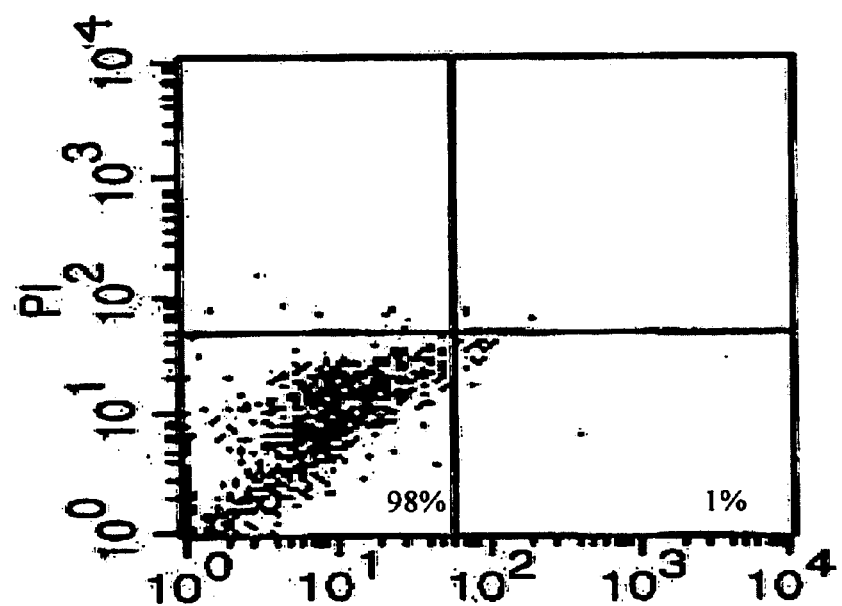
FIGS. 7A and 7B are flow cytometry profiles of HUVEC cultured in cytophobic plates for 1 hour (FIG. 7A) and 24 hours (FIG. 7B).
Figure 7B:
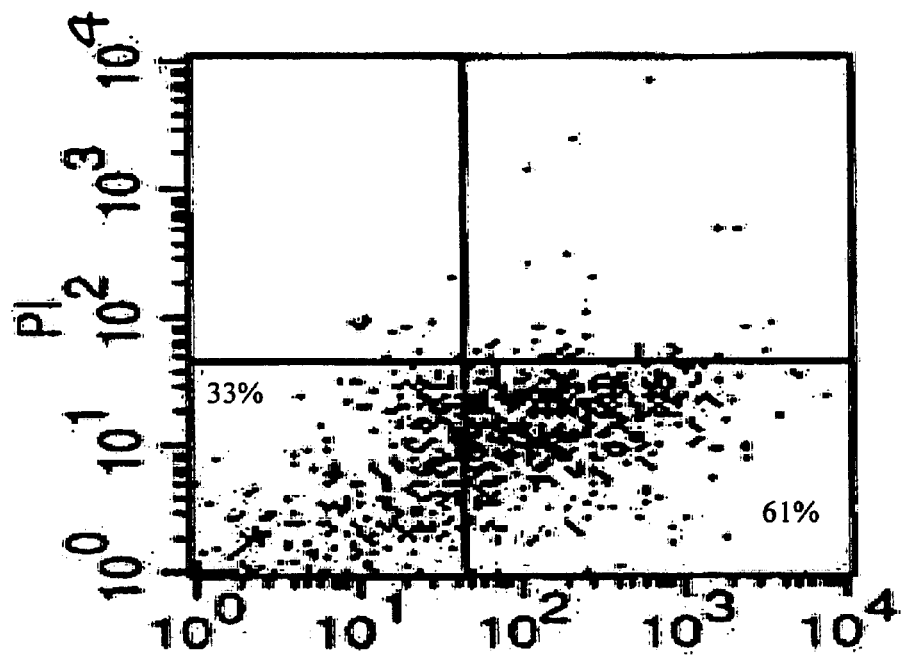
Figure 8A:
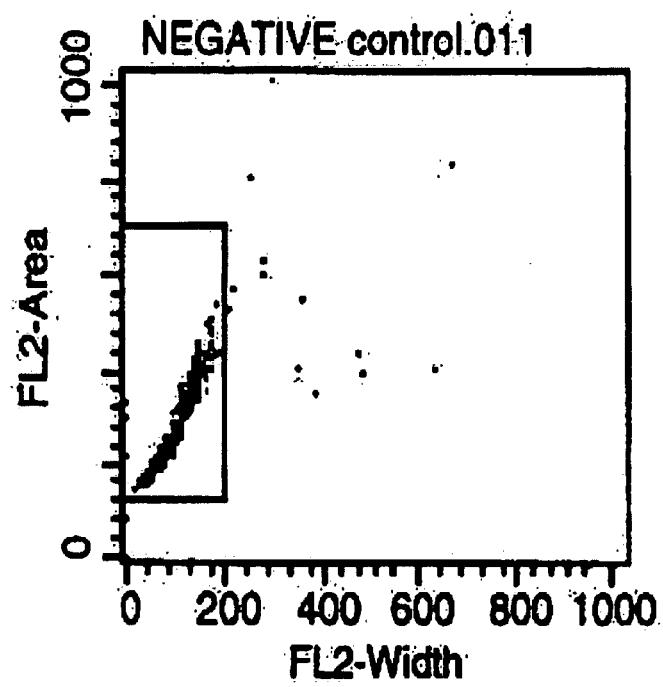
FIGS. 8A through 8D are APO-DIRECT measurements of late apoptotic events in HUVEC that were incubated on collagen I in the presence of 1 $\mu$M docetaxel.
Figure 8B:
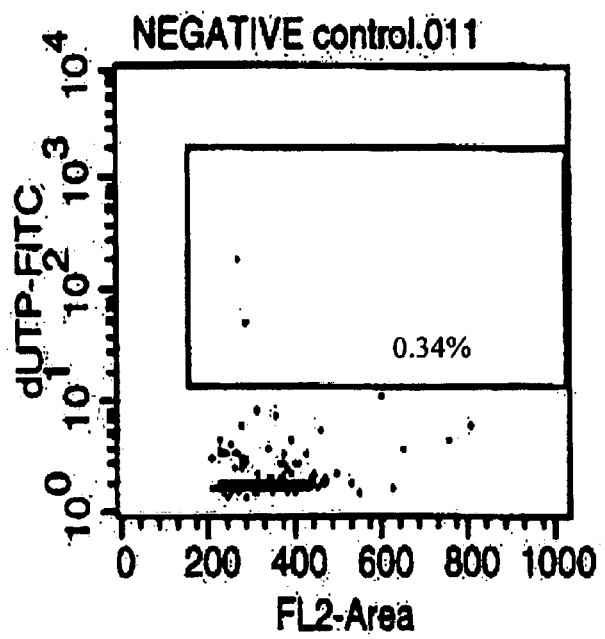
Figure 8C:
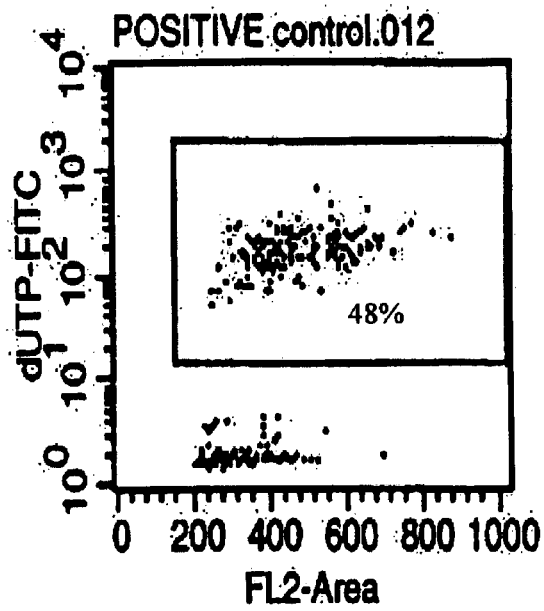
Figure 8D:
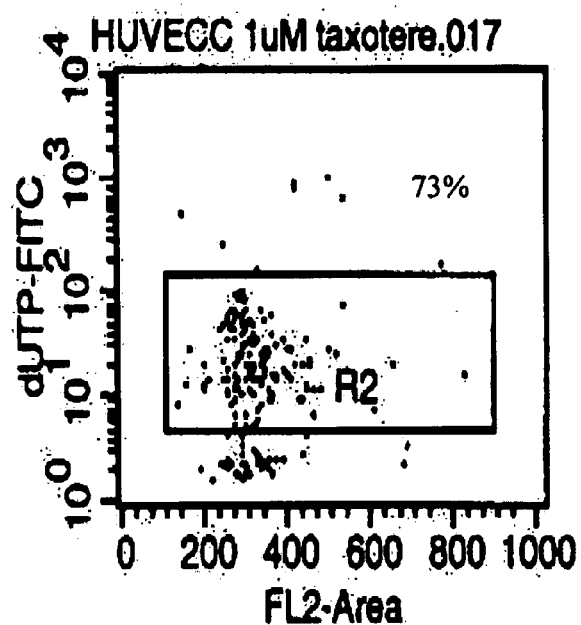

As an example, HUVEC cells were cultured on collagen I and treated with 0.0011 µM mM docetaxel and then stained with both Annexin V and PI. Annexin V binding and PI staining of nuclei were documented for the same cell population using the PharMingen Annexin V flow cytometry assay and two-color immunofluorescence on live HUVEC monolayers. Staining with Annexin V-FITC was visible on the membrane as green fluorescence, and PI staining was visible in the nucleus as red fluorescence. Intact viable cells were not stained with Annexin V and did not uptake PI. As shown in FIG. 6, 80% of the cells were intact, 3.5% of the cells were undergoing apoptosis, and 16% of the cells were dead due to either apoptosis or necrosis. In a separate experiment, HUVEC cells were transferred into Ultra Low Attachment 24-well plates (Corning, Inc., Corning N.Y.) covered with a layer of hydrogel that is hydrophilic and neutrally charged. The hydrogel surface inhibits non-specific immobilization, and therefore subsequent cell attachment, because proteins and other biomolecules passively adsorb to surfaces through hydrophobic and ionic interactions. Because of the lack of appropriate ECM providing anti-apoptotic signals, HUVEC undergo rapid apoptosis under these culture conditions. For example, 24 hours after their transfer into Ultra Low Attachment plates, 61% of HUVEC cells were undergoing an (Annexin V-positive, PI-negative) apoptotic process (shown in FIG. 7).

(2) APO-DIRECT Assay

The APO-DIRECT assay (Phoenix Flow Systems, San Diego, Calif.) utilizes single step fluorescent labeling and flow cytometric analysis by taking advantage of the multitude of 3'-hydroxyl termini of DNA present in apoptotic cells. One of the hallmarks of cellular self-destruction by apoptosis is the activation of nucleases that degrade the higher order chromatin structure of the DNA into fragments of 50 to 300 kilobases. These DNA fragments result in the appearance of "DNA laddering" when the DNA is analyzed by agarose gel electrophoresis. (Arends et al., 1990, *Am. J. Pathol.* 136:593–608). Apoptotic cells were identified by labeling the 3'-hydroxy ends of double- and single-stranded DNA breaks with fluorescent-tagged deoxyuridine triphosphate nucleotides (F-dUTP) using the enzyme deoxynucleotidyl transferase (TdT). Non-apoptotic cells did not incorporate significant amounts of the F-dUTP due to the lack to exposed 3'-hydroxyl DNA ends. The APO-DIRECT assay identified cells undergoing apoptosis at a later stage of programmed cell death than assays based on Annexin V binding.

In these experiments, HUVEC were incubated on collagen I for 48 hours in the presence of 1 µM docetaxel. The cells were fixed in paraformaldehyde and stored at −20° C. until use. PI uptake (measuring amount of DNA) and FITC staining (measuring amount of DNA breaks in apoptotic cells) were used as FL1 and FL3 fluorescent markers. The gating display was created according to Phoenix Flow protocol using Linear Red Fluorescence (DNA) on the X-axis and Log green Fluorescence (d-UTP) on the Y-axis. As a negative control, untreated HL-60 cells stained with d-UTP and PI were used, and as a positive control, HL-60 cells treated with TPA were used. As shown in FIG. 8, in these experiments 73% of HUVEC that were cultured on collagen I and treated with 1 µM docetaxel had undergone apoptosis after 48 hours of incubation with the drug.

Immunoseparation of Endothelial Cells

Attempts at immunoseparation of VEC have been described in the art. (Mechetner et al., 2001, *Proc. Annu.*

*Meet Am. Assoc. Cancer Res.* 42:566; Hewett et al., 1993, *In Vitro Cell Dev. Biol.* 29A:823–830). Two complementary approaches were used to separated VEC from other cells. The first approach included cell enrichment and sterile separation using immunomagnetic beads conjugated with mAbs against VEC membrane differentiation markers (e.g., CD31 antigen, CD105 antigen) or mAbs recognizing membrane antigens that could be used for negative selection of VEC from mixed cell populations (e.g., CD45). The second approach included sterile flow sorting of mixed cell population containing VEC using a FACSVantage flow sorter, as described below.

Immunomagnetic isolation using magnetic beads provides a simple and reliable method for positive or negative isolation and enrichment of VEC that are present at low concentrations (<1%) in mixed cell populations. Dynabeads (Dynal, Oslo, Norway) are highly uniform, supermagnetic polystyrene spheres coated with mono- or polyclonal antibodies. Antibodies can be conjugated with immunobeads either directly via covalent bonds or indirectly, via a DNA linker, allowing for the release of isolated cells from the beads upon capture using DNase-releasing buffer. The released populations of endothelial cells can be subsequently verified for purity, cultured in different growth environments as described above, and re-analyzed using mAbs against VEC differentiation markers and/or functional test as described above. As an example of negative selection, Dynabeads conjugated with mouse mAb against human CD45 were used for CD31- and/or CD105 antigen-positive subsets of hematopoietic cells contaminating tumor cell specimens (macrophages, granulocytes, lymphocytes).

Figure 9A:
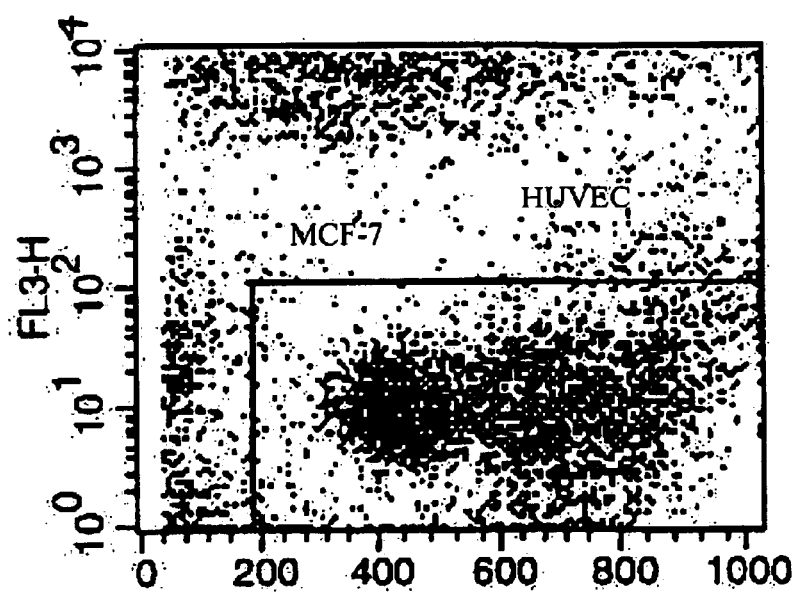
FIG. 9A is a forward/side scatter plot of a 1:1 mixed cell population containing HUVEC and human breast carcinoma MCF-7 cells depicting relatively small MCF-7 cells and relatively large HUVEC.
Figure 9:
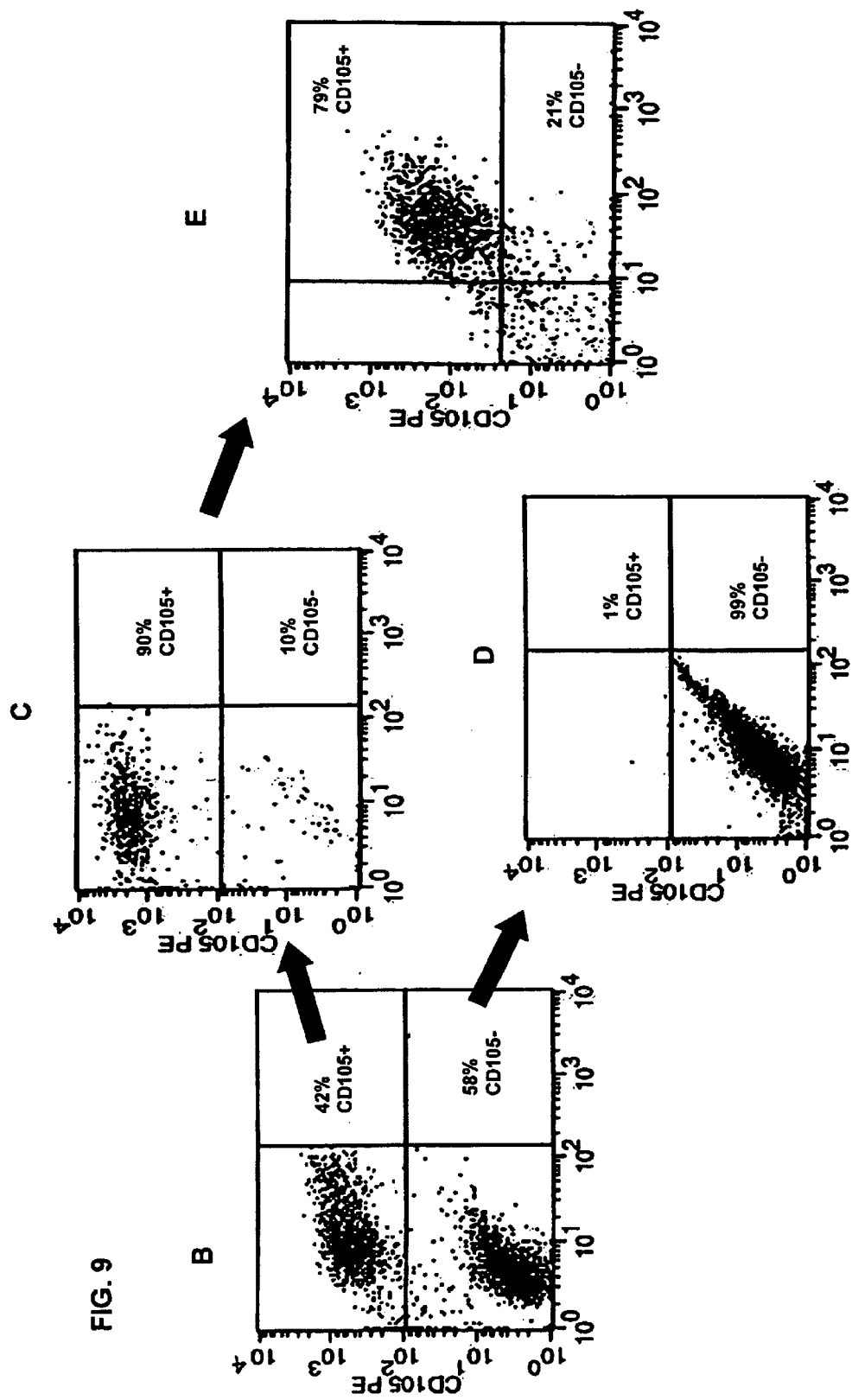
FIGS. 9B through 9E are flow cytometry profiles of immunoseparation of a 1:1 mixed cell population containing HUVEC and human breast carcinoma MCF-7 cells.

Mixtures of HUVEC and human breast carcinoma MCF-7 cells were used to develop and validate a protocol for immunomagnetic separation of VEC from mixed single cell populations derived from human tumors. The CELLection Pan Mouse IgG Kit (Dynal) was used in these studies. HUVEC were pre-mixed with MCF-7 cells at the 1:1 ratio, stained with unlabeled anti-CD105 antigen mAb (Becton Dickinson), washed and analyzed by flow cytometry to verify the CD105 antigen positivity of HUVEC and CD105 antigen negativity of MCF-7, as described below. The mixture was separated under sterile conditions using Dynabeads conjugated with polyclonal anti-mouse IgG antibodies, the unbound (CD105-negative) cells and the bound (CD105-positive) cells were separately collected. The bound cells were released from the beads using the DNase buffer. Aliquots from both cell suspensions were then analyzed by flow cytometry for the expression of CD105 antigen. 90% of positively selected cells were CD105 antigen-positive, while 99% of the negatively selected population was CD105-negative. Both populations were plated on Becton Dickinson BIOCOAT flasks covered with collagen I 48 hours after plating and analyzed by flow cytometry for CD105 antigen expression and by immunofluorescence for Dil-ac-LDL uptake. As shown in FIG. 9, no CD105 antigen expression and no Dil-ac-DLD uptake was found in negatively selected cells, while 79% of positively selected cells expressed CD105 antigen on the membrane and actively took up Dil-ac-LDL. No CD45-expressing cells were found in the positively selected population by flow cytometry.

Figure 10:
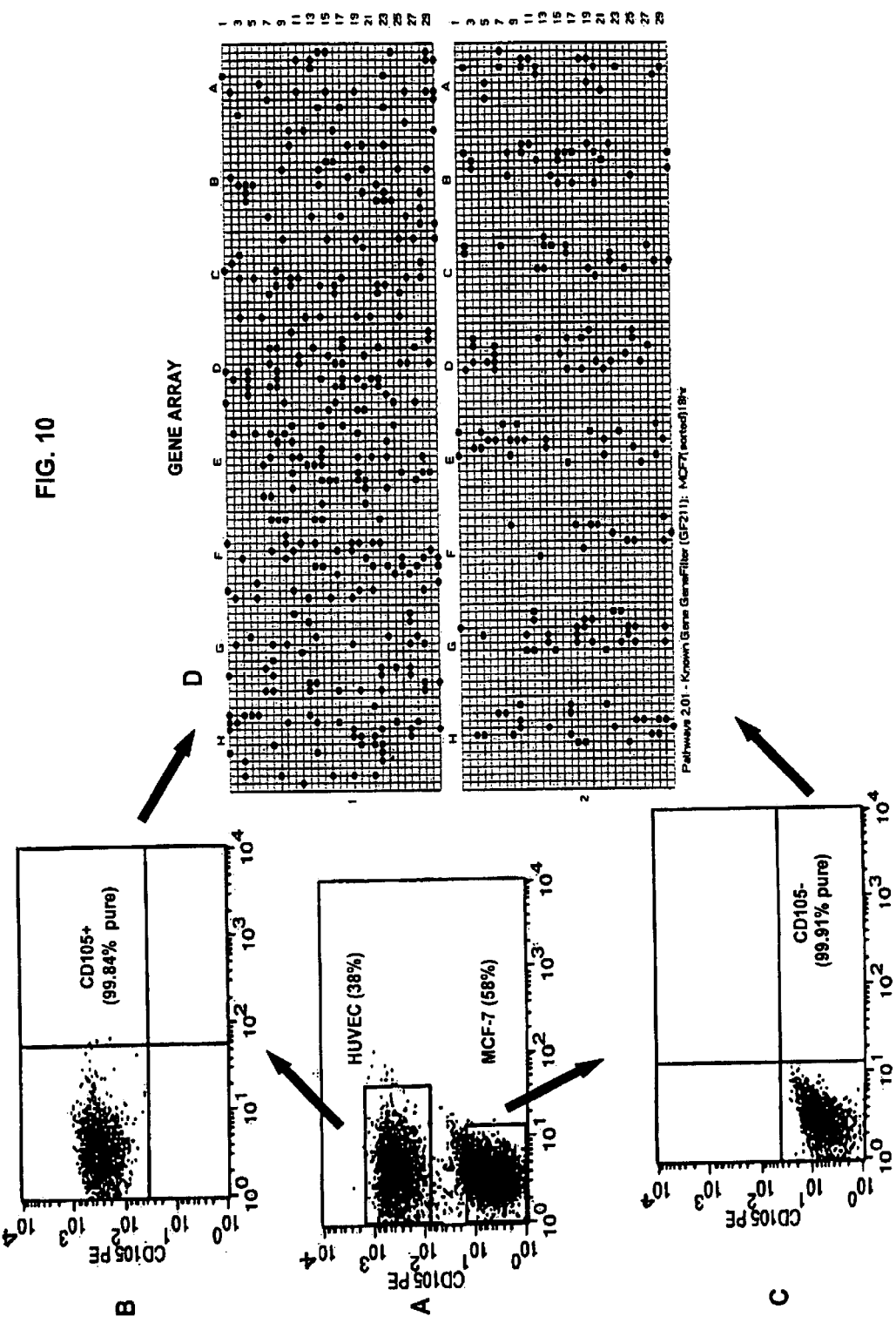
FIG. 10A is a flow cytometry profile of a 1:1 mixed population containing HUVEC and MCF-7 cells.
FIGS. 10B and 10C shows flow cytometry analysis for CD105 expression of aliquots of CD105-positive (FIG. 10B) and CD105-negative (FIG. 10C) sorted cell populations.
FIG. 10D is a schematic diagram of the results of gene expression microarrays preformed to compare CD105-positive and CD105-negative populations. These results demonstrated differential patterns of gene expression between these two populations.

Using a complementary approach, a FACSVantage Turbosort flow cytometer was used to achieve highly efficient VEC immunoseparation. A 1:1 mixture of HUVEC and MCF-7 cells was analyzed before sorting for CD105 antigen expression, and the two cell populations (CD105+and CD105−) were identified and gated individually. A sterile flow sort was then performed based on CD105 antigen staining. CD105 antigen-positive and CD105 antigen-negative cells were collected in two separate tubes and re-analyzed for CD105 antigen expression. In these experiments, the purity in CD105+ and CD105− sorted populations were 99.84% and 99.91%, respectively, as shown in FIG. 10. Total RNA preparations were then isolated from these cells and analyzed using human gene arrays, as described below.

While flow cytometry-based sorting was highly efficient and reproducibly isolated purified (>99%) VEC, this technique can be time-consuming, particularly when sorting rare events. Because the percentage of VEC does not exceed 1% in the vast majority of clinical specimens, tumor samples are enriched by the use of immunomagnetic separation, subsequently followed by flow sorting. In this combined approach, tumor cell suspensions containing <1% of VEC is first enriched by one or two orders of magnitude using immunobeads and then subjected to highly efficient flow cytometry sorting procedures that yield >99% pure cell populations. Pure VEC, as well as sorted cells that are negative for endothelial differentiation markers, are further analyzed by morphological, functional and molecular biology techniques.

Effects of Anti-Angiogenesis Drugs on HUVEC

The differential effects of anti-angiogenesis agents on HUVEC cells grown on type I collagen was demonstrated with docetaxel and thalidomide. The impact of drug exposure on morphology, cells surface biomarker expression, and apoptosis was evaluated by looking at HUVEC morphology and functional behavior. mAbs against VEC markers can be used to alter angiogenesis in vivo. Several anti-endoglin (CD105 antigen) conjugates with ricin A-chain (Matsuno et al, 1999, *Clin. Cancer Res.* 5:371–382) or $^{125}$I (Tabata et al., 1999, *Int. J. Cancer* 82:737–742) showed specific anti-angiogenic activity on human xenografts in nude mice.

Figure 11:
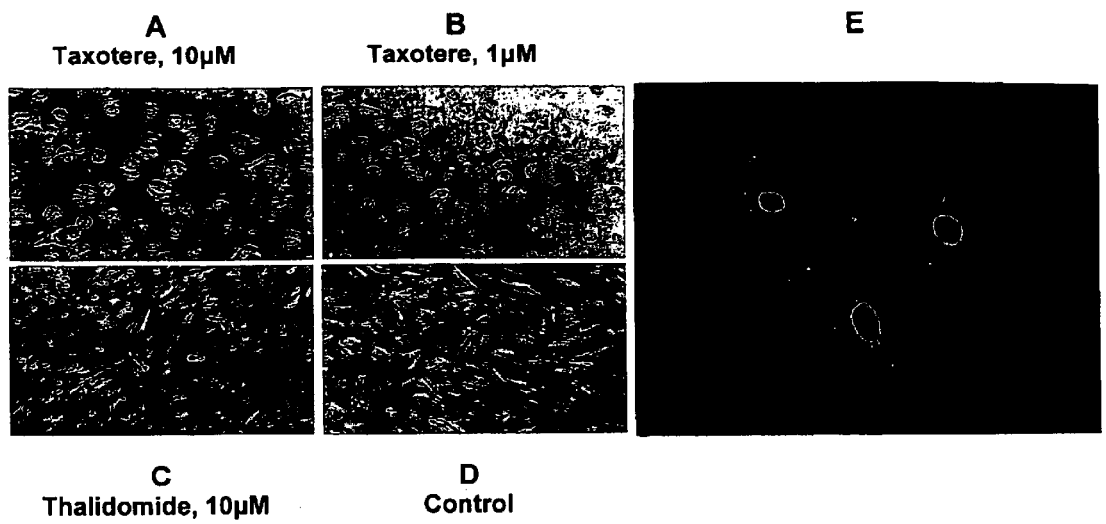
FIGS. 11A through 11D are phase contrast photomicrographs of HUVEC cultured for 48 hours on collagen I and treated with 10 $\mu$M docetaxel (FIG. 11A), 1 $\mu$M docetaxel (FIG. 11B), 10 $\mu$M thalidomide (FIG. 11C), or an untreated control (FIG. 11D).
FIG. 11E is an immunofluorescent photomicrograph of apoptotic HUVEC cultured on collagen in the presence of 10 $\mu$M docetaxel and stained with Annexin V-FITC and PI.
Figure 12:
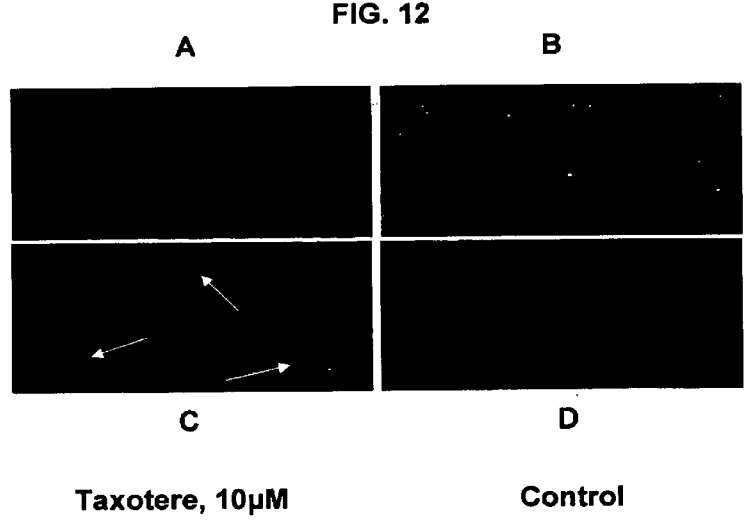
FIGS. 12A though 12D are immunofluorescent photomicrographs of HUVEC cultured on collagen I for 48 hours and treated with 10 $\mu$M docetaxel (FIG. 12A (low magnification, ×150) and FIG. 12B (high magnification, ×900)) or untreated (FIG. 12C (low magnification, ×150) and FIG. 12D (high magnification, ×900)).

HUVEC were cultured for 48 hours on collagen I and treated with either 10 $\mu$M docetaxel, 1 $\mu$M docetaxel, or 10 $\mu$M thalidomide. The effect on cell morphology was observed by phase contrast microscopy. In addition, apoptotic HUVEC cultured on collagen in the presence of 10 $\mu$M docetaxel were stained with AnnexinV-FITC (green fluorescence) and PI (red fluorescence) and visualized with immunofluorescent photomicrography. In results shown in FIG. 11, rounded and partially detached HUVEC were observed in docetaxel-treated monolayers, while thalidomide had no effect on HUVEC morphology. In a separate experiment, the effects of docetaxel on Dil-ac-LDL uptake by HUVEC cultured on collagen I for 48 hours was observed, as seen in FIG. 12. In these experiments, very few docetaxel-treated HUVEC took up DIL-as-LDL after drug treatment. An atypical pattern of Dil-ac-LDL accumulation in drug-treated cells was observed under high magnification.

Figure 13:
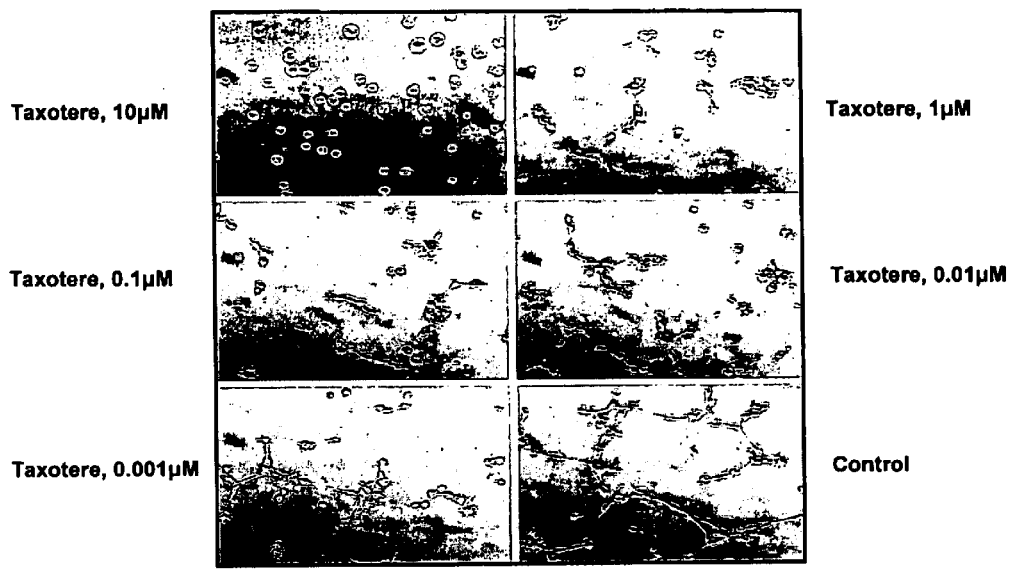
FIGS. 13A and 13B are phase contrast photomicrographs of HUVEC tubulogenesis on MATRIGEL three hours after cell transfer and after culturing with either docetaxel (taxatere) (FIG. 13A) or Thalidomide (FIG. 13B) at different concentrations.
Figure 13:
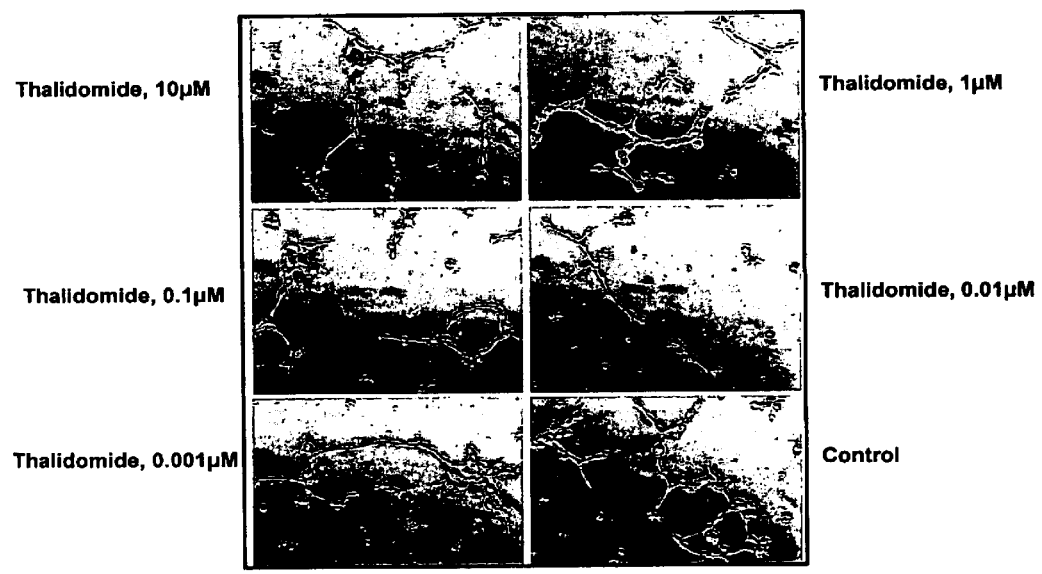

The effects on HUVEC tubulogenesis on MATRIGEL was observed for different concentrations (10, 1, 0.1, 0.01, and 0.001 $\mu$M) of docetaxel (taxotere) and thalidomide. Observations were made three hours after cell transfer, as seen in FIG. 13. There was a complete absence of VEC-like tubules in HUVEC treated with 10 $\mu$M docetaxel, while inhibited tubulogenesis and capillary-like network formation was observed with lower docetaxel doses. No effects of thalidomide on HUVEC tubulogenesis on MATRIGEL were observed at these does.

Endothelial Cells Derived from Fresh Human Samples

Human VEC from freshly resected human tumor specimens were sorted, cultured, and analyzed. Tumor samples ($\geq$5 g) from patients with different tumor types, including ovarian (35), uterine (4), sarcoma (3), kidney (2), NHL (2), breast (2), head & neck (1), melanoma (1), lung (1), vaginal (1), and unknown primary site (5), were evaluated by flow cytometry to estimate the percentage of VEC in fresh specimens from different tumor types, determined by measuring the expression of CD31 and CD105 antigen (Table 1). Endothelial cells were sorted and cultured in type I collagen when endothelial cell content was adequate, as determined by cell surface labeling with CD31 antigen, CD105 antigen, and VEGFR-1. Although the incidence of CD31 and CD105 antigen expressing cells were low (1.62%, 0.66%, and 0.566%), the one sample t test showed that they were significantly different from 0 (P values were 0.0012, <0.0001, and <0.0001, respectively) (Table 1)

TABLE 1

Statistical analysis by the one sample t test of three-color flow staining on 57 fresh tumor specimens for the expression of CD31 and CD105 ANTIGEN. Dead cells were excluded using PI. No CD45 staining was performed in this experiment. Therefore, some macrophages and leukocytes expressing CD31 and/or CD105 ANTIGEN may be included in the analysis.

| Markers | % of Total | Hypothetical Mean | P value |
|---|---|---|---|
| CD31−/CD105+ | 1.62 ± 3.52 | 0 | 0.0012 |
| CD31+/CD105− | 0.660 ± 0.864 | 0 | <0.0001 |
| CD31+/CD105+ | 0.566 ± 0.650 | 0 | <0.0001 |
| CD31−/CD105− | 95.4 ± 13.5 | 100 | 0.0146 |

Human VEC cells were enriched using immunomagnetic beads and flow-cytometry-based sorting. Dead cells were excluded from flow analysis and sorting by PI staining. Potential contamination with hematopoietic cells expressing CD31 or CD105 antigen (including macrophages and leukocytes) was prevented using negative selection based on the staining by a pan-hematopoietic anti-CD45 mAb. The endothelial nature of human VEC derived from fresh tumor specimens was demonstrated by post-flow cytometry analysis and culturing VEC in different growth environments combined with post-culture morphological and functional tests.

Figure 14:
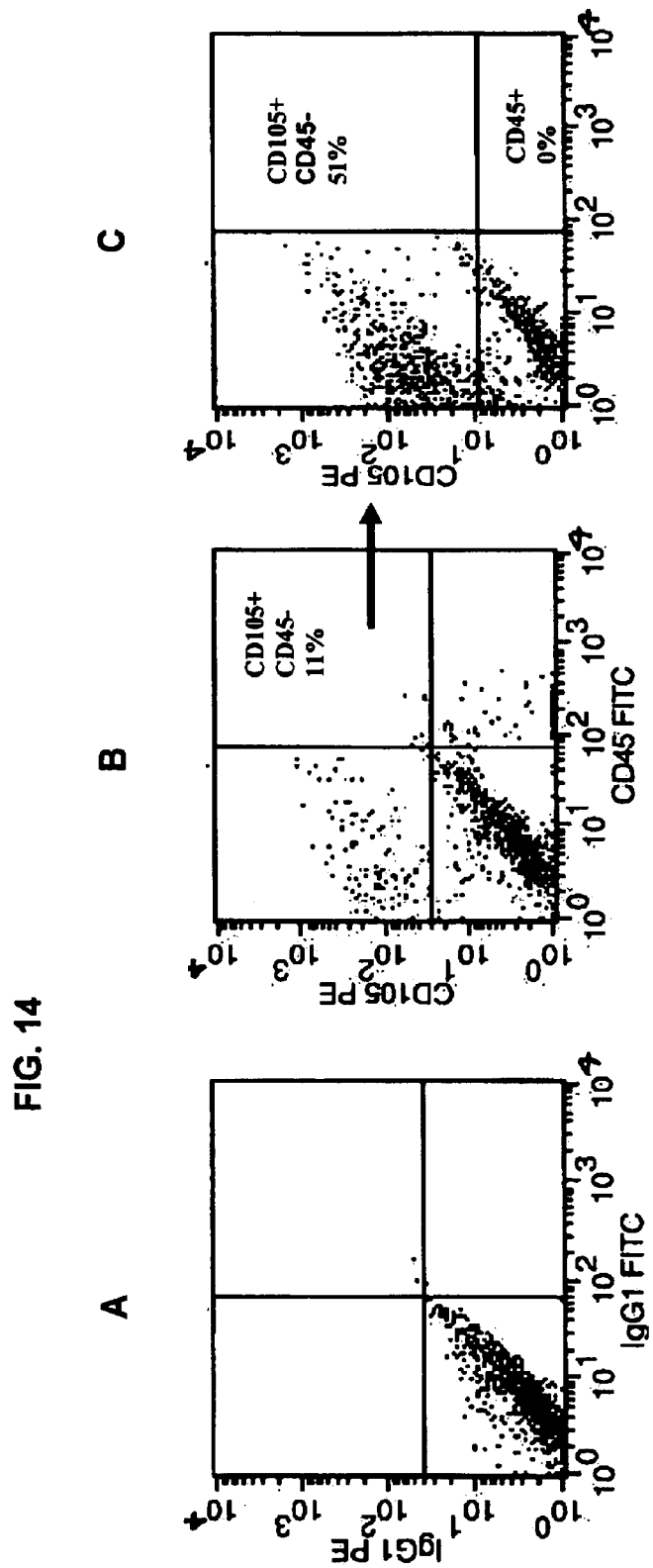
FIGS. 14A–14B are flow cytometry profiles of an original ovarian carcinoma specimen using IgG1-FITC/IgG1-PE control staining (FIG. 14A) and CD45-FITC/CD105 ANTIGEN-PE staining (FIG. 14B).
FIG. 14C is a flow cytometry profile using CD45-FITC/CD105 antigen-PE staining of cells purified from the specimen following CD105 ANTIGEN directed-immunomagnetic separation.
FIG. 14D is an immunofluorescent photomicrograph of immunomagnetically separated CD105+CD45-cells cultured on fibronectin for two days and showing retention of CD105 antigen immunofluorescent staining.
Figure 14D:

As an example of immunomagnetic separation, human VEC was enriched from an ovarian carcinoma specimen. The original tumor specimen was analyzed by flow cytometry using IgG1-FITC/IgG1-PE control staining, and CD45-FITC/CD105-PE staining. 11% of the population was CD105-positive, CD45-negative, while 5% was CD105-positive, CD45-positive. CD105 antigen-positive cells were separated from this sample using CD105 antigen staining followed by incubation with anti-mouse IgG Dynabeads, with subsequent release of separated cells from the beads. Flow cytometry analysis of the resulting cell suspension showed that 51% of the cell population expressed the CD105+CD45− phenotype, while no CD45-positive cells were found in the sample. The presence of CD105 antigen immunofluorescent staining of CD105+CD45− cells cultured on fibronectin for 2 days was observed (shown in FIG. 14).

Figure 15:
FIGS. 15A and 15B are a pre-sort flow cytometry analysis of a uterine carcinoma specimen stained with either IgG-FITC and IgG-PE (FIG. 15A) or with CD31-FITC and CD105-PE (FIG. 15B).
FIGS. 15C and 15D demonstrate flow cytometry results of cells after having undergone positive sorting for CD31 and CD105 antigen (FIG. 15C) or negative sorting CD31-CD105– (FIG. 15D). post-sorting flow cytometry analyses using, with staining of CD31 and CD105 antigen, of either the positively selected cells (FIG. 15C) or negatively selected cells (FIG. 15D) after sorting of cells in the specimen based on co-expression of CD31 and CD105 antigen.
FIGS. 15E and 15F are immunofluorescent photomicrographs of CD31 antigen immunofluorescence (FIG. 15E) or CD105 ANTIGEN immunofluorescence (FIG. 15F) of sorted CD31+CD105+ VEC cultured on fibronectin for two days.
Figure 15:

As an example, of flow cytometry sorting, human VEC was enriched from a fresh tumor specimen of a carcinoma of the uterus. A presort flow analysis by flow cytometry, with control staining with IgG-FITC and IgG-PE, and with staining of CD31 and CD105 ANTIGEN, 0.62% of live cells were CD31 antigen-positive, CD105 antigen-positive. Dead cells were excluded by PI. After sorting based on the co-expression of CD31 and CD105 antigen, the purity of positively selected cells was 88%, and the purity of negatively selected cells was 99.9%. CD31 and CD105 antigen immunofluorescence demonstrated the endothelial nature of sorted CD31+CD105+ VEC cultured on fibronectin for 2 days (shown in FIG. 15).

Figure 16:
FIG. 16 is a photograph of an agarose gel electrophoretic analysis of RNA integrity. Lane 1 is specimen #20011030141, Lane 2 is specimen #2001010606, Lane 3 is #2001020595, and Lane 4 is mixed ladder (110 bp+1 kb).
Figure 15:
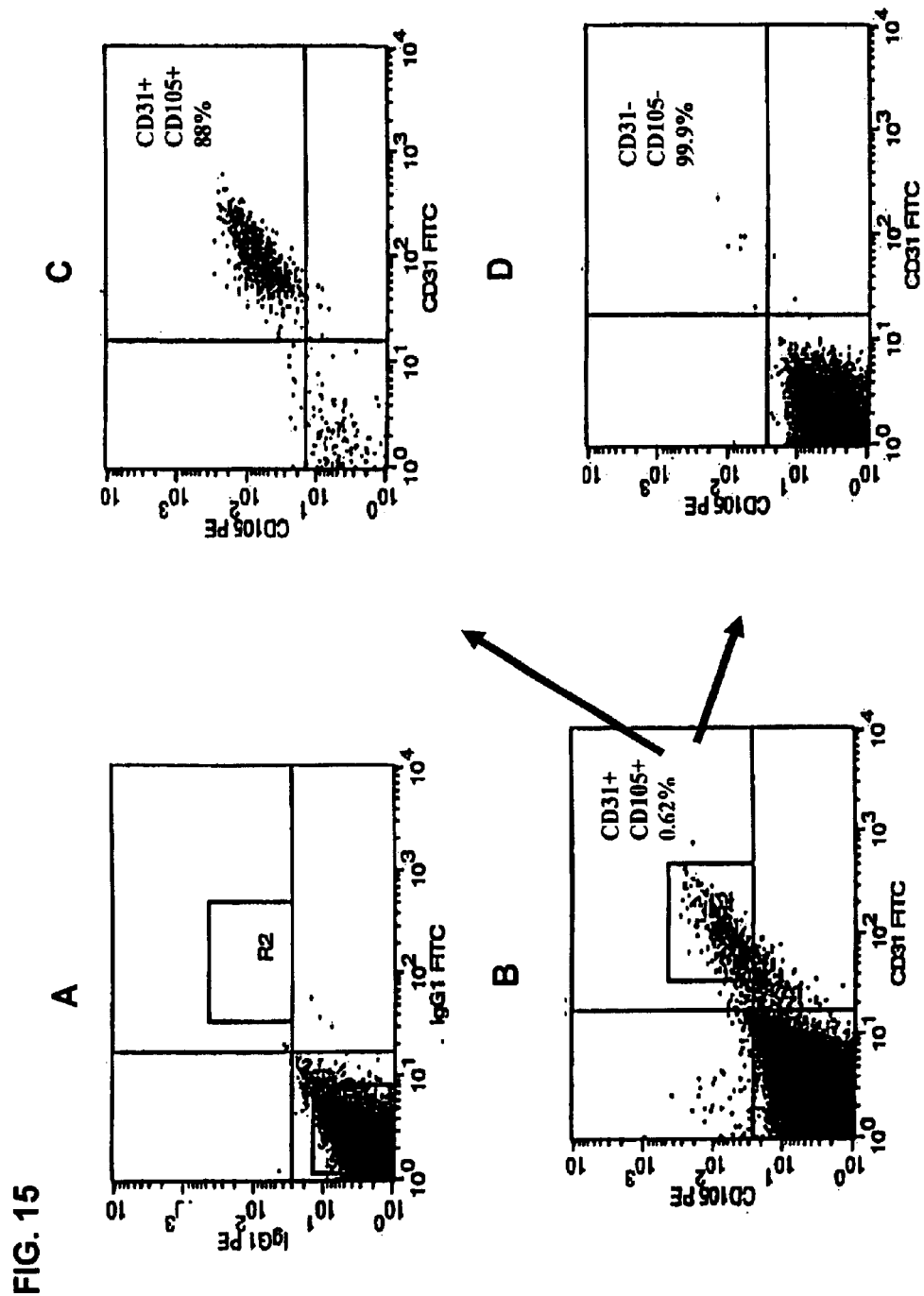

As another example, long-term VEC cultures were established that were derived from endothelial cells obtained from 10 fresh ovarian tumor specimens. First, total RNA was isolated from approximately $12 \times 10^6$ sorted (CD31+CD105+) viable cells (Table 2). RNA samples from three specimens (115 μg of RNA for specimen 2001020595, 65 μg of RNA for specimen 2001010606, and 54 μg of RNA for specimen 2001030141) were isolated., and the integrity of the purified sample was viewed with EtBr staining of a 1.2% agarose gel, as shown in FIG. 16. The integrity of the RNA was monitored to ensure that microarray experiments could be performed. Second, a portion of sorted VEC from fresh ovarian specimens ($5 \times 10^5$ viable cells) was cultured in vitro for over six weeks. Three out of ten specimens grew successfully in E-STIM cultures on 150 $cm^2$ Collagen I coated flasks. Subsequent analysis using surface marker and functional markers confirmed the endothelial nature of these cultures.

TABLE 2

Total RNA isolation from VEC separated by flow cytometry from three fresh ovarian tumor specimens

| Sample ID | CD105 ANTIGEN Staining | CD45 Staining | ac-LDL Binding | MATRIGEL Tube Formation | Total RNA Isolated (μg) |
|---|---|---|---|---|---|
| #2001020595 | 98% | negative | 100% | positive | 115 |
| #2001010606 | 97% | negative | 100% | positive | 65 |
| #2001030141 | 99% | negative | 100% | positive | 54 |

Microarray Analysis

Figure 17:
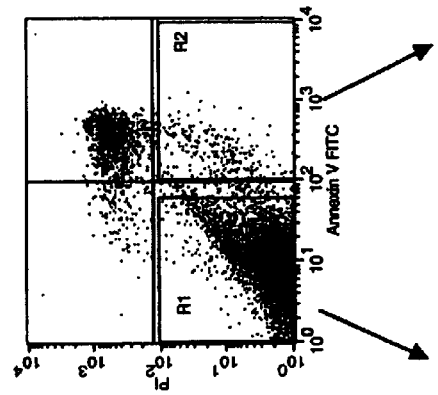
FIGS. 17A and B are fluorescence-activated cell sorting profiles of VEC from specimen #2002020595 cultured with either 0.1 μM Docetaxel (FIG. 17A) or 50 μM BSO (FIG. 17B). VEC were first sorted using Annexin V-FITC and PI (upper panels), and then re-analyzed for the purity of sorted Annexin V– (resistant) and Annexin V+ (sensitive) cell populations (lower panels).
Figure 17:
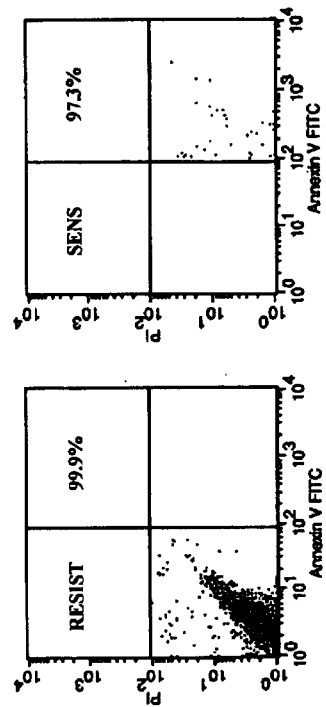
Figure 17:
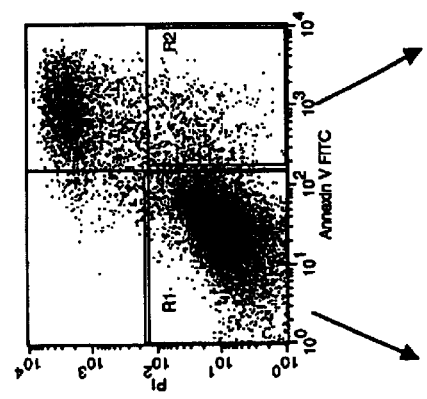
Figure 17:
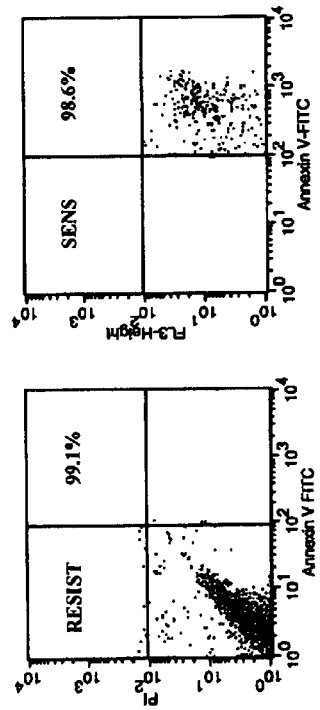
Figure 18:
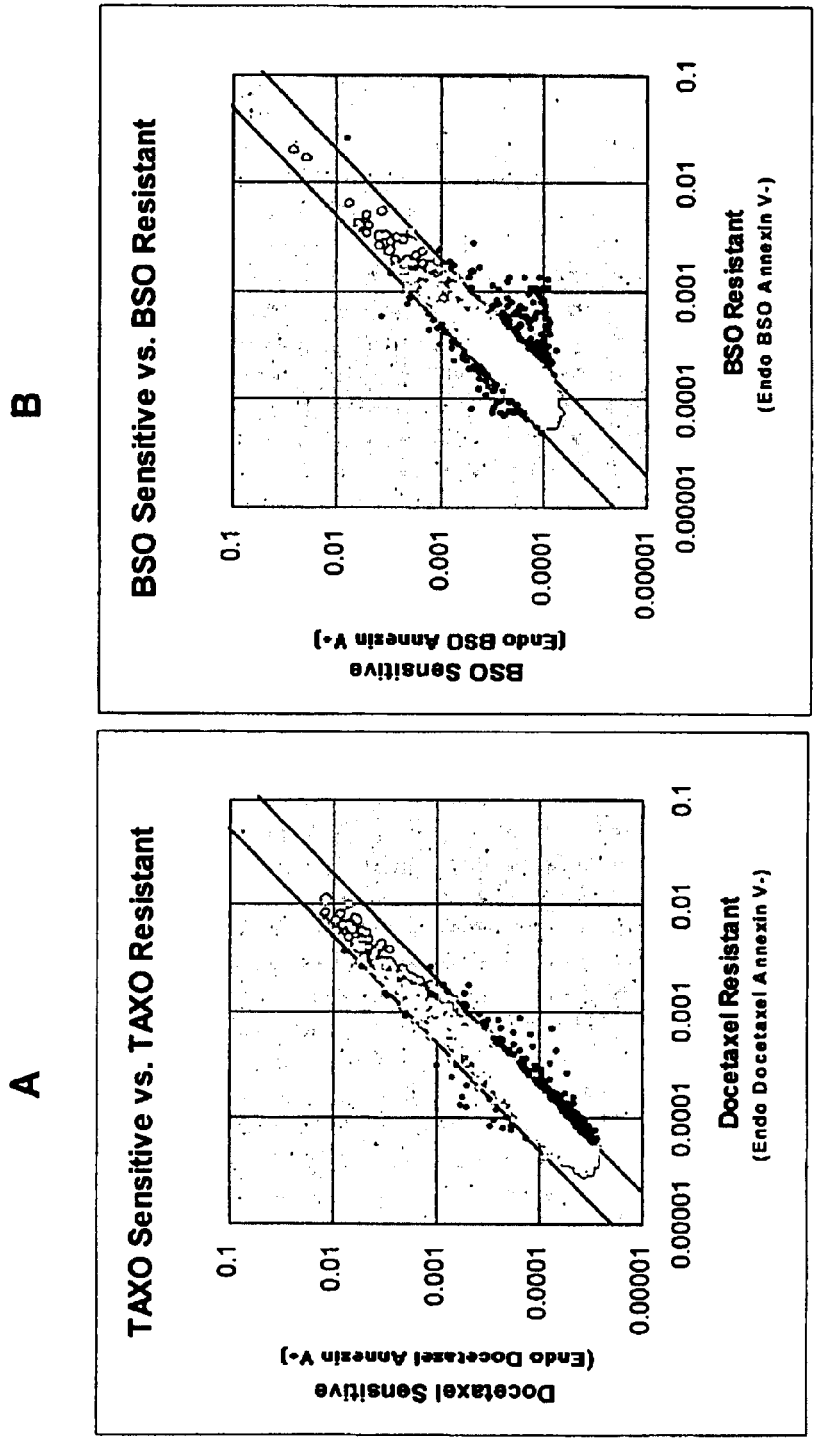
FIGS. 18A and 18B are scatter plots of intensity values from RG microarrays normalized by converting to the fraction of total intensity and then log transformed.

Anti-angiogenesis agents were screened using highly purified populations of endothelial cells derived from fresh tumor specimens. $2 \times 10^7$ VEC that were sorted for the expression of CD31 and CD105 endothelial markers were exposed to 0.1 μM docetaxel or 50 μM BSO, a proprietary drug. Docetaxel has been demonstrated to have anti-angiogenesis activity. After 24 hours of drug exposure in cytophobic plates, VEC were sorted under sterile conditions using the above Annexin V-flow cytometry protocol. To ensure the purity of sorted VEC, the sorted populations were reanalyzed by flow cytometry for Annexin V and PI staining, as shown in FIG. 17. The purity of the sorted VEC populations varied between 97.3% and 99.1%. Total RNA was isolated from both resistant (Annexin V−/PI−) and sensitive (Annexin V+/PI−) populations, and cDNA probes were hybridized with Research Genetics GeneFilters© microarrays containing over 40,000 known human gene sequences. In order to compare the microarray results for the drug-resistant sample to the drug-sensitive sample, FIG. 18 is a two-dimensional scatter plot constructed of intensity values from the microarrays normalized by converting to the fraction of total intensity and then log transformed, which was used to compare the microarray results for the resistant and sensitive sample. Diagonal lines were utilized that separated the genes that have more than a 2-fold difference in expression level.

187 sequences associated with VEC resistance and 22 sequences associated with VEC sensitivity were identified in docetaxel-treated populations. 129 sequences associated with VEC resistance and 74 genes associated with VEC sensitivity were identified in BSO-treated populations. The top 5 genes exhibiting the highest expression levels in the resistant and sensitive VEC populations treated with the two drugs are presented in Table 3.

TABLE 3

Differential gene expression in resistant versus sensitive VEC populations.

| | DOCETAXEL | | BSO | |
|---|---|---|---|---|
| | Gene | Ratio | Gene | Ratio |
| RESISTANT | Interferon regulatory factor 5 | 4.4 | Acyl-coenzyme A dehydrogenase, long chain | 14.7 |
| | Keratin, type I cytoskeletal 14 | 4 | Human regulator of G-protein signaling | 12.3 |
| | Small proline-rich protein 1B (cornifin) | 3.6 | ATPase, Na + K + transporting, beta 2 polypeptide | 12.3 |
| | Human HLK1 mRNA, complete cds | 3.6 | Human fetus brain mRNA for membrane glycoprotein | 11.6 |
| | Tuberin | 3.2 | Human homeobox protein (HOX-11) mRNA | 10.8 |
| SENSITIVE | Human mucosal addressin cell adhesion molecule | 9.5 | Stress-activated protein kinase | 6.3 |
| | Human metallothionein (MT)I-F gene | 6.2 | Oxyglutarate dehydrogenase (lipoamide) | 6.2 |
| | Human TWIK-related acid-sensitive K + channel gene | 5.9 | Human podocalyxin-like protein mRNA | 4 |
| | Human putative fatty acid desaturase | 5.2 | Hepsin | 3.9 |
| | Fibrinogen beta-chain precursor | 4.9 | Amylo-1,6-glucosidase, 4-alpha-glucanotransferase | 3.5 |

Example 2
Tumor Specimen Handling

The microarray experimentation utilizes large ovarian tumor specimens of 5 grams or more. Fresh ovarian tumors are used, but viable ovarian specimens stored in a tumor bank can be used if fresh samples are unavailable. Viable tumors are placed in transport media (complete medium, defined within as RPMI-1640 supplemented with 10% fetal calf serum and the antibiotics penicillin and streptomycin immediately after collection. The tumor is processed by removing three areas of the tumor from the sample, fixing these portions of the sample in Formalin, and then preparing paraffin embedded, sectioned and Hematoxylin and eosin stained sections for pathologists' review to ensure the histological diagnosis.

The remainder of the sample is processed by flow cytometry sorting to obtain pure VEC populations. The presence and viability of malignant cells in the specimen is determined by light microscopic examination of a sample of the cells prepared from tumor cell suspensions placed onto a slide and stained with Hematoxylin-Eosin.

Tumor Cell Suspensions

The tumor sample is disaggregated and processed into a single cell suspension for preparing purified populations of VEC. Tumors are cut with scissors into pieces of 2 mm or smaller in a Petri dish containing 5 mL of complete medium. The resultant slurries are mixed with complete media containing 0.03% DNase (2650 Kunitz units/ml) and 0.14% collagenase I (both enzymes from Sigma Chemical Co., Saint Louis, Mo.), placed into 50 mL Erlenmeyer flasks with stirring, and incubated for 90 minutes at 37° C. under a humidified 5% $Co_2$ atmosphere. After enzymatic dispersion into a near single cell suspension, tumor cells are filtered through nylon mesh, and washed in complete medium. A portion of the cell suspension is used for cytospin slide preparation and stained with Wright-Giemsa in parallel with Hematoxylin-Eosin stained tissue sections to confirm the diagnosis and to determine the tumor cell count and viability.

Flow Sorting of Pure VEC Populations

The cell suspension is immediately sorted under sterile conditions to separate viable endotbelial (defined as CD31+ CD105+CD45-PI-) cells from other cells in the suspension. mAbs used for VEC separation include: CD31-FITC (Serotec Ltd., Kindlington, UK), CD105 ANTIGEN-PE (Serotec), CD45-APC (BD Pharmingen, San Diego, Calif.), and their isotype controls, IgG1-FITC (Serotec), IgG1-PE (Serotec), and IgG1-APC (BD Pharmingen). Cells are stained with mAbs for 30 minutes at 4° C., washed with cold PBS+1% FBS, and resuspended at $5 \times 10^6$ cells/ml in PBS containing 1 µg/ml propidium iodide (PI). Cells are subsequently sorted on a Becton Dickinson FACSVantage cell sorter equipped to sort cell populations based on six parameters. FITC (FL1), PE (FL2), and PI (FL3) are excited by the primary argon ion laser, while APC is excited by the secondary HeNE laser. At least 10,000 events are acquired in the "list" mode, and flow cytometry data is analyzed using CellQuest software (Becton Dickinson) as described above. The gating strategy negatively selects for hematopoietic cells that may express CD31 and/or CD105 antigen by gating out CD45-positive cells. In addition, dead cells are excluded from the sorting procedure by gating out PI-positive events. All mAb solutions, media, and buffers used in the sorting procedure are sterilized by filtration through low protein binding 0.22 µm cellulose acetate filters (Millipore, Bedford, Mass.).

Tumor VEC Cultures

Sorted tumor-derived VEC are maintained at 37° C. and 50% $CO_2$ in the E-STIM medium in Collagen I-coated BIOCOAT flasks (Becton Dickinson) as described above. The medium is supplemented with 20% FBS, 0.1 mg/mL heparin, and 30 µg/mL endothelial cell growth supplement (Sigma). Cells are passaged at log phase. Sorted VEC cultures that show little or no growth after two weeks in culture are discarded, and corresponding total RNA samples are excluded from the analysis. The endothelial nature of tumor-derived VEC is confirmed for each culture using: (1) VEC surface marker expression (CD31 and CD105 antigen); (2) DIL-ac-LDL binding, and (3) endothelial network formation in MATRIGEL.

Treatment with SU5416 and SU6668

To approximate the in vivo growth environment for the growth of VEC in vitro, Ultra Low Attachment 24-well plates (Costar, N.Y.) are used to grow isolated VEC. Costar Ultra Low Attachment Plates possess a covalently bound hydrogel layer that effectively inhibits cellular attachment. This surface minimizes protein absorption, enzyme activation, and cellular activation. The surface is non-cytotoxic, biologically inert, and non-degradable.

This hydrogel surface inhibits non-specific immobilization of anchorage-dependent tumor cells via hydrophobic and ionic interactions and creates an in vitro environment for culturing sorted and expanded VEC in organoid cultures. Culture conditions for endothelial cells treated with the two Sugen compounds have been described previously (Mendel et al., 2000, *Anticancer Drug Design* 15:29–41; Laird et al., 2000, *Cancer Res.* 60:4152–4160). Tyrosine phosphorylation is stimulated by the addition of 500 ng/mL human recombinant VEGF (PeproTech, Inc., Rocky Hill, N.J.). Expanded VEC are plated in 24-well cytophobic plates at 200,000 cells per well and treated at the predetermined $IC_{50}$ concentrations with SU5416 at 1 µM (Mendel et al., 2000, *Anticancer Drug Design* 15:29–41) and SU6668 at 0.34 µM (Laird et al., 2000, *Cancer Res.* 60:4152–4160). Cells are exposed to the drugs for 72 hours, collected by pipetting, washed with PBS with 1% FBS, and sorted on the basis of Annexin V binding as described. The composition and uses of the cytophobic plate assay for culturing tumor-derived cells in the presence of anti-tumor or anti-angiogenic compounds with subsequent flow cytometry analysis of drug treated cell populations have previously been disclosed in co-owned and co-pending U.S. patent application Ser. No. 09/705,320, incorporated by reference herein.

Annexin V Flow Sorting

Multi-parameter Annexin V flow sorting has been described previously (Mechetner et al., 2001, *Proc. Annu. Meet. Am. Assoc. Cancer Res.* 42:566; Mechetner et al., 1998, *Clin. Cancer Res.* 4:389–398). VEC harvested from cytophobic plates are immediately analyzed on a Becton Dickinson FACSVantage flow cytometer equipped with a Coherent Enterprise laser tuned to 488 nm. Forward scatter, side scatter, FL-1 (FITC, fluorescein isothiocyanate, indicator molecule for Annexin V), and FL-3 (PI, propidium iodide, marker of dead cells) parameter data is collected in "list" mode using the CellQuest flow cytometry software (Becton Dickinson). The following controls are used to set up compensation and quadrants: (1) unstained cells (autofluorescence control); (2) Annexin V staining only (no PI); and (3) PI staining only (no Annexin V). Washed cells are mixed with FITC-conjugated Annexin V (PharMingen, San Diego, Calif.; 5 µL of the probe per $1\times10^5$ cells) and/or PI (10 µL of 50 µg/ml stock solution per $1\times10^5$ cells), gently vortexed and incubated at room temperature (20–25° C.) in the dark for 15 minutes. Annexin V- and PI-labeled cells are re-suspended in 1× binding buffer provided by PharMingen and sorted on the FACSVantage, as recommended by the manufacture. The separated cell populations include: Annexin V-positive, PI-negative (sensitive cells), and Annexin V-negative, and PI-negative (resistant cells). At least $5\times10^6$ sorted cells are collected in 3 mL plastic tubes, and purity (>95%) and viability (>95%) of the sorted populations are confirmed using flow cytometry analysis of a small sample of sorted cells additionally stained with PI.

Microarray Experimentation $10^6$ sorted tumor cells are used to isolate at least 20 µg of total RNA using TRIzol® reagent (Life Technologies TM, Rockville, Md.) according to the manufacture's protocol. The yield and purity of total RNA preparations is determined spectrophotometrically and verified in agarose gel electrophoresis using the two ribosomal RNA bands as an indicator of molecular integrity. In one application of the technology, GeneFilters® (Research Genetics) membranes are washed for at least 5 minutes with gentile agitation in a boiling (95–100° C.) solution of 0.5% SDS to remove manufacturing residuals and are then prehybridized in 5 mL of Micro-Hyb hybridization solution (Research Genetics) with 5.0 µg Cot-1 DNA, used as a blocker for repeat sequences that decreases the background of hybridizations, (Human Cot-1 DNA, Life Technologies) and 5.0 µg poly dA (1 µg/uL, Research Genetics) in a roller oven (Hybaid, Midwest Scientific St. Louis, Mo.) at 42° C. for 4 to 6 hours. For each labeling, total RNA corresponding to 1 µg is reverse transcribed in the presence of 10 µL of $^{33}$P dCTP (10 mCi/mL with a specific activity of 3000 Ci/mmol, ICN Radiochemicals, Costa Mesa, Calif.), 2.0 µL oligo dT (1 µg/µL of 10–20 mer mixture, Research Genetics), and 300 units of Reverse Transcriptase (Superscript II, Life Technologies). The samples are incubated for 90 minutes at 37° C., and cDNA probes are purified by passaging through a Bio-Spin 6 chromatography column (Bio-Rad, Hercules, Calif.) to remove any unincorporated nucleotides. The cpm counts of the probes are measured to confirm successful labeling. The GeneFilters® membrane are hybridized with the probes overnight (12–18 hours) at 42° C. in a hybridization roller oven at 8–10 rpm. The membranes are then washed twice with 30 mL of 2×SSC containing 1% SDS at 50° C. for 20 minutes and once with 30 mL of 0.5×SSC containing 1% SDS at 55° C. for 15 minutes in hybridization oven at 12–15 rpm. After washing, the GeneFilter® membrane is placed on a filter paper moistened with deionized water and wrapped with a plastic film.

GeneFilters® membranes are then exposed overnight to a Packard phosphor imaging screen and scanned at 600 dpi resolution in a Cyclone phoshor imaging system (Packard Instrument Co., Meriden, Conn.). Resulting images in the tiff format are directly imported into the image analysis software Pathways® 3 (Research Genetics). The software uses control spots present throughout the filter to align the images and performs auto-centering of the spots.

Statistics

The gene array data is collected, organized, and interpreted using the Pathways 3 software package from Research Genetics, Inc. (Huntsville, Ala.). The statistical approach to gene profiling correlates specific gene expression levels with the expression of genes involved in normal and abnormal angiogenesis (Bussolino et al., 1997, *Trends Biochem. Sc.* 22:251–256; Folkman, 1995, *Nat. Med.* 1:27–31; Saaristo et al., 2001, *Oncogene* 19:6122–6129). Specific gene expression profiles revealed in sorted VEC treated with, for example, SU5416 and SU6668 are correlated with the expression of human genes linked to different angiogenesis signaling pathways, such as the PDGF cascade retrieved from the CGAP database. For example, changes in the pattern of gene expression caused by SU6668, a specific inhibitor of the PDGF tyrosine kinase (as opposed to the molecular mechanism of action of SU5416) can be compared both to the baseline gene expression profiles, and, to SU5416-induced gene expression profiles in all 15 tumor-derived VEC cultures. This allows the identification of specific genes linked to the effects of SU6668.

Correlative statistics and data reduction techniques are applied to decrease the gene expressions' dimension. The resulting data are analyzed by regression methods. Cluster analysis included in the Pathways 3 software can identify expression patterns of groups of genes.

The analysis of the data is performed with the Instat GraphPad V3.0 and Prism V3.0 (both from GraphPad Software, Inc., San Diego, Calif.), SigmaPlot (SPSS, Inc., Chicago, Ill.), and other statistical and graphical packages, and the data is organized in Microsoft Excel worksheets. The nonparametric Mann-Whitney test or the Welch corrected T test are used to perform unpaired tests for comparing medians in all flow and tissue culture experiments; the Wilcoxon matched pairs test or the paired t test are used on matched samples. Pearson or nonparametric Spearman correlation algorithms are used to calculate correlations between the tests for sample populations with Gaussian and non-Gaussian distributions, respectively. Contingency tables containing test-positive and test-negative results are analyzed using the chi-square statistics. Two-tailed p values are obtained.

It should be understood that the foregoing disclosure emphasizes certain specific embodiments of the invention and that all modifications or alternatives equivalent thereto are within the spirit and scope of the invention as set forth in the appended claims.

We claim:

1. A method for determining a gene expression profile of vascular endothelial cells from a mixed population after the vascular endothelial cells are exposed to an anti-angiogenic agent, the method comprising the steps of:

(a) contacting a mixed population of cells with a vital stain or fluorescent dye;
   (b) contacting said mixed population of cells with a detectable immunological reagent that specifically binds to vascular endothelial cells;
   (c) selecting the cells in said mixed population that bind the immunological reagent and that are not stained with the vital stain or fluorescent dye;
   (d) exposing the selected cells of step (c) to an anti-angiogenic agent;
   (e) isolating cellular RNA from the selected cells selected in step (c);
   (f) preparing detectably labeled cDNA or cRNA from the cellular RNA isolated in step (e);
   (g) hybridizing the cDNA or cRNA prepared in step (f) to a gene array comprising a plurality of eukaryotic genes; and
   (h) determining a gene expression profile from the hybridization pattern produced using the cDNA or cRNA preparations in step (g).

2. The method of claim 1, wherein the gene array of (g) comprises at least 3000 human genes.

3. The method of claim 1, wherein the gene array of (g) comprises at least 13,000 human genes.

4. The method of claim 2, wherein the immunological reagent is a vascular endothelial cell-specific antibody.

5. The method of claim 4, wherein the vascular endothelial cell-specific antibody binds to CD31 or CD105 antigen.

6. The method of claim 5, wherein the vascular endothelial cell-specific antibody is conjugated to beads, and wherein the cells that bind the immunological reagent are selected by collecting the beads.

7. The method of claim 5, wherein the cells that bind the immunological reagent are selected by fluorescence-activated cell sorting.

* * * * *